US010540765B2

(12) United States Patent
Kanda et al.

(10) Patent No.: US 10,540,765 B2
(45) Date of Patent: Jan. 21, 2020

(54) IMAGE PROCESSING DEVICE, IMAGE PROCESSING METHOD, AND COMPUTER PROGRAM PRODUCT THEREON

(71) Applicant: Olympus Corporation, Hachioji-shi, Tokyo (JP)

(72) Inventors: Yamato Kanda, Hino (JP); Takashi Kono, Hachioji (JP)

(73) Assignee: Olympus Corporation, Tokyo (JP)

( * ) Notice: Subject to any disclaimer, the term of this patent is extended or adjusted under 35 U.S.C. 154(b) by 120 days.

(21) Appl. No.: 15/787,759

(22) Filed: Oct. 19, 2017

(65) Prior Publication Data

US 2018/0040127 A1 Feb. 8, 2018

Related U.S. Application Data

(63) Continuation of application No. PCT/JP2015/062428, filed on Apr. 23, 2015.

(51) Int. Cl.
*G06K 9/00* (2006.01)
*G06T 7/00* (2017.01)
*A61B 1/00* (2006.01)
*G06K 9/32* (2006.01)

(52) U.S. Cl.
CPC ........ *G06T 7/0014* (2013.01); *A61B 1/00009* (2013.01); *G06K 9/3241* (2013.01); *G06T 2207/10068* (2013.01); *G06T 2207/10081* (2013.01); *G06T 2207/30028* (2013.01); *G06T 2207/30096* (2013.01)

(58) Field of Classification Search
None
See application file for complete search history.

(56) References Cited

U.S. PATENT DOCUMENTS

| 9,412,054 B1* | 8/2016 | Krupnik ............. A61B 1/00009 |
| 2005/0010082 A1 | 1/2005 | Nishimura et al. |
| 2007/0173690 A1 | 7/2007 | Hirokazu et al. |
| 2007/0179338 A1 | 8/2007 | Nishimura et al. |
| 2007/0191679 A1 | 8/2007 | Nishimura et al. |
| 2007/0191681 A1 | 8/2007 | Hirokazu et al. |
| 2009/0074270 A1 | 3/2009 | Tanaka et al. |

(Continued)

FOREIGN PATENT DOCUMENTS

| CN | 102436650 A | 5/2012 |
| JP | 2003-093328 | 4/2003 |

(Continued)

OTHER PUBLICATIONS

English Translation of International Search Report dated Jul. 14, 2015 mail received for PCT/JP2015/062428; pp. 2.

(Continued)

*Primary Examiner* — Stephen P Coleman
(74) *Attorney, Agent, or Firm* — Matthew M. Eslami

(57) ABSTRACT

An image processing device includes at least one processor having hardware. The processor is configured to implement analyzing, in an intraductal image which is an image of inside of a duct, an intraductal imaging situation based on a position of a subject relative to a part that captures an image of the subject. Next, the processor is calculating a plurality of specific region discrimination indices for the intraductal image. Finally, the processor is detecting a specific region by integral determination on the plurality of specific region discrimination indices depending on the intraductal imaging situation.

22 Claims, 26 Drawing Sheets

(56) References Cited

U.S. PATENT DOCUMENTS

| | | |
|---|---|---|
| 2012/0002879 A1 | 1/2012 | Kanda et al. |
| 2012/0076419 A1 | 3/2012 | Kono et al. |
| 2012/0288199 A1 | 11/2012 | Kanda et al. |
| 2013/0044927 A1 | 2/2013 | Poole |
| 2014/0028821 A1* | 1/2014 | Tanaka .................... A61B 1/05 |
| | | 348/65 |
| 2015/0003742 A1 | 1/2015 | Tani |
| 2015/0080651 A1 | 3/2015 | Azuma |
| 2015/0254826 A1 | 9/2015 | Kanda et al. |
| 2015/0282887 A1 | 10/2015 | Yamada |
| 2016/0014328 A1 | 1/2016 | Rokutanda |

FOREIGN PATENT DOCUMENTS

| | | |
|---|---|---|
| JP | 2007-244519 | 9/2007 |
| JP | 2012-011137 | 1/2012 |
| JP | 2012-073953 | 4/2012 |
| JP | 2012-238041 | 12/2012 |
| JP | 2013-039344 | 2/2013 |
| JP | 2014-104293 | 6/2014 |
| JP | 2014-188223 | 10/2014 |
| JP | 2015-008782 | 1/2015 |
| WO | 2013/180147 | 12/2013 |
| WO | 2014/103237 | 7/2014 |

OTHER PUBLICATIONS

English Translation of the Written Opinion dated Jul. 14, 2015 mail received for PCT/JP2015/062428; pp. 3.
Office action dated Nov. 2, 2018 for the corresponding Chinese application CN2015-80079117.6.

* cited by examiner

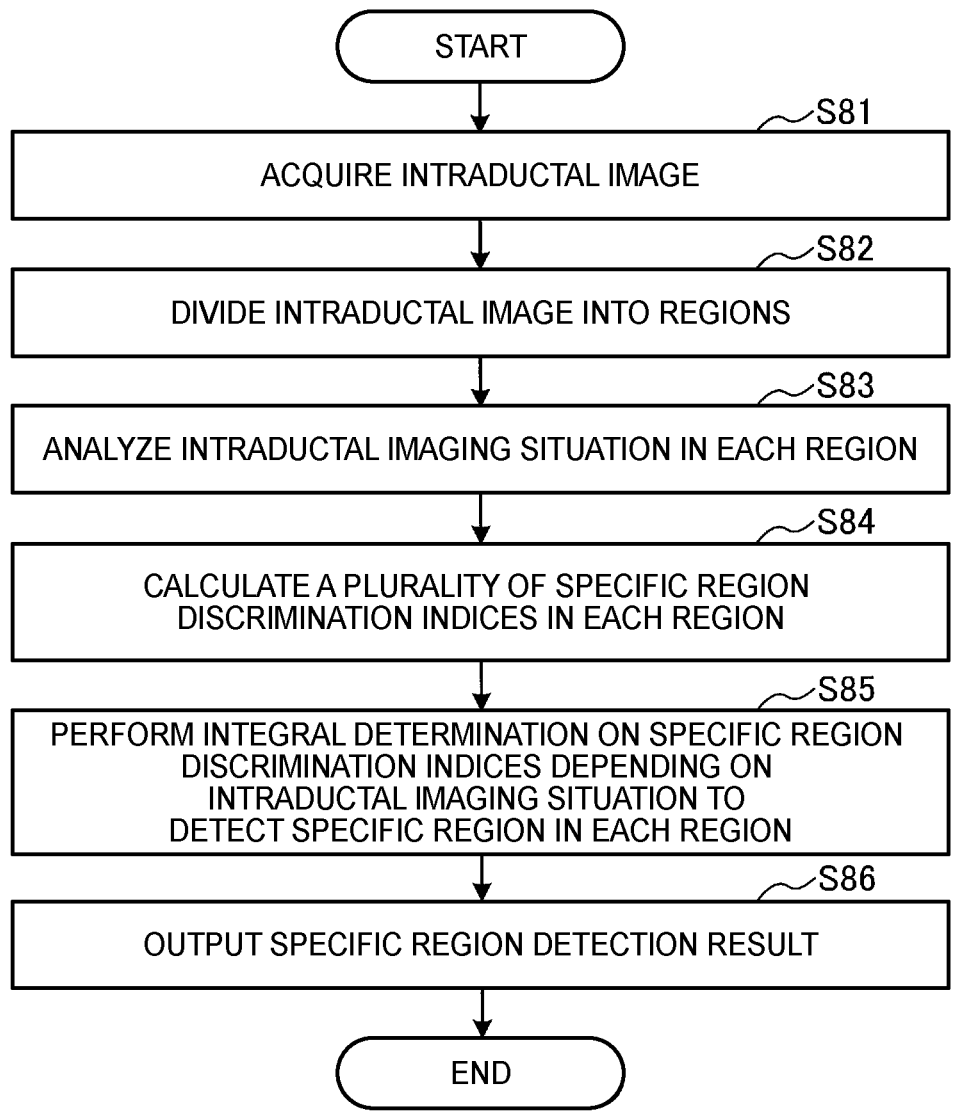

IMAGE PROCESSING DEVICE, IMAGE PROCESSING METHOD, AND COMPUTER PROGRAM PRODUCT THEREON

CROSS-REFERENCE TO RELATED APPLICATION(S)

This application is a continuation application of PCT Application No. PCT/JP2015/062428 filed Apr. 23, 2015, which is hereby incorporated by reference in its entirety.

TECHNICAL FIELD

The present disclosure relates to an image processing device, image processing method, and image processing program for performing image processing on intraductal images.

BACKGROUND

Conventionally disclosed techniques detect an abnormal region in a living body based on pixel value gradient information, i.e. a pixel value surface shape feature value, in an endoscopic image, or detect an abnormal region based on edge information, i.e. a contour feature value, in an endoscopic image. Japanese Patent Application No. 2007-244519 discloses techniques that an abnormal region is detected by evaluating the isotropy of the pixel value gradient, that is, whether or not the gradient is equal in all directions, or evaluating whether or not the edge shape is a circular arc of a predetermined size.

SUMMARY

Example embodiment of the present disclosure relates to an image processing device. The image processing device comprises at least one processor comprising hardware. The hardware is configured to implement for analyzing, in an intraductal image which is an image of inside of a duct, an intraductal imaging situation based on a position of a subject relative to a part that captures an image of the subject. Next, the image processing device calculates a plurality of specific region discrimination indices for the intraductal image and finally, the image processing device detects a specific region by integral determination on the plurality of specific region discrimination indices depending on the intraductal imaging situation.

Example embodiment of the present disclosure relates to an image processing method comprises at least one processor having hardware, executes for analyzing, in an intraductal image which is an image of inside of a duct, an intraductal imaging situation based on a relationship between a subject and a part that captures an image of the subject. Next, the image processing method calculates a plurality of specific region discrimination indices for the intraductal image and finally, the image processing method detects a specific region by integral determination on the plurality of specific region discrimination indices depending on the intraductal imaging situation.

Example embodiment of the present disclosure relates to a computer program product including a non-transitory computer readable medium having computer program code encoded thereon that when executed by a processor of a computer causes the computer to perform the operations of: analyzing, in an intraductal image which is an image of inside of a duct, an intraductal imaging situation based on a position of a subject relative to a part that captures an image of the subject, and then calculating a plurality of specific region discrimination indices for the intraductal image and finally, detecting a specific region by integral determination on the plurality of specific region discrimination indices depending on the intraductal imaging situation.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every Figure. The drawings are not necessarily to scale, emphasis instead being placed upon illustrating embodiments, principles, and concepts. The structural elements having the same functions are given the same reference signs throughout the drawings. Thus, features and advantages of the present disclosure will become more apparent from the following detailed description of exemplary embodiments thereof taken in conjunction with the accompanying drawings.

FIG. 30 is a flowchart illustrating the process performed by the image processing device according to the fourth Embodiment.

DETAILED DESCRIPTION

The Japanese Patent Application No. 2007-244519 discloses, endoscopic images that include images captured under various imaging situations, such as an image of a ductal inner wall captured from the front, side, a long distance, a short distance, defocused, and/or with motion blur. Since the manner in which a predetermined specific region such as, for example, an abnormal region appears in an image varies depending on the imaging situation, there is a problem in the detection performance that is not improved when the same detection technique is used without taking such variations into account.

In view of the above, the present disclosure is directed to providing an image processing device, image processing method, and image processing program capable of accurately detecting a specific region inside an enclosure such as a duct and/or the ductal inner wall.

According to the present disclosure, the specific region inside the duct is detected by the integral determination on the specific region discrimination indices depending on the intraductal imaging situation. The specific region inside the duct can thus be detected accurately.

The following describes modes (hereafter referred to as "embodiments") for carrying out the present disclosure, with reference to the aforementioned drawings.

Figure 1:
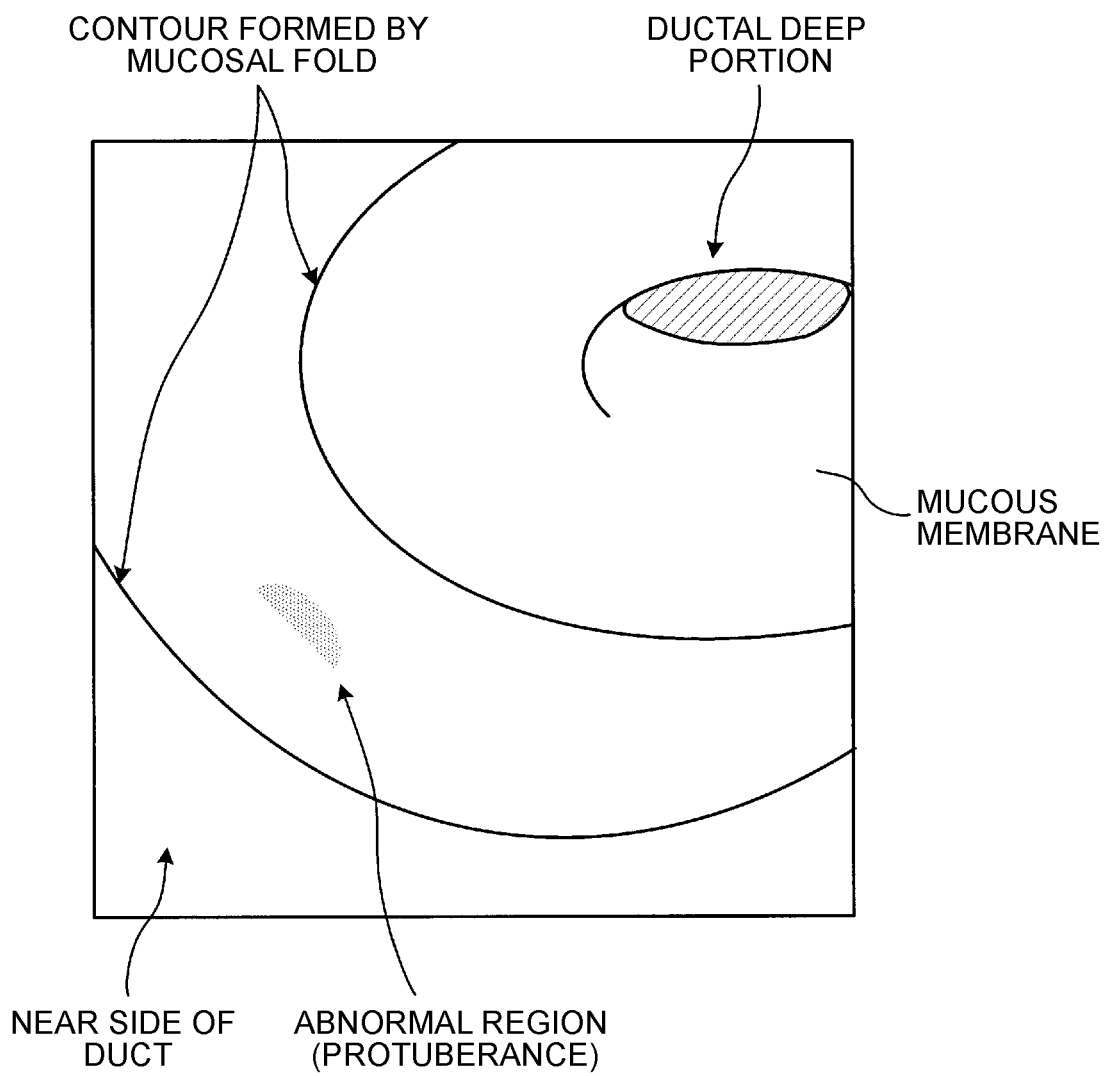
FIG. 1 is a first exemplary diagram for describing a first situation of the present disclosure.
Figure 2:
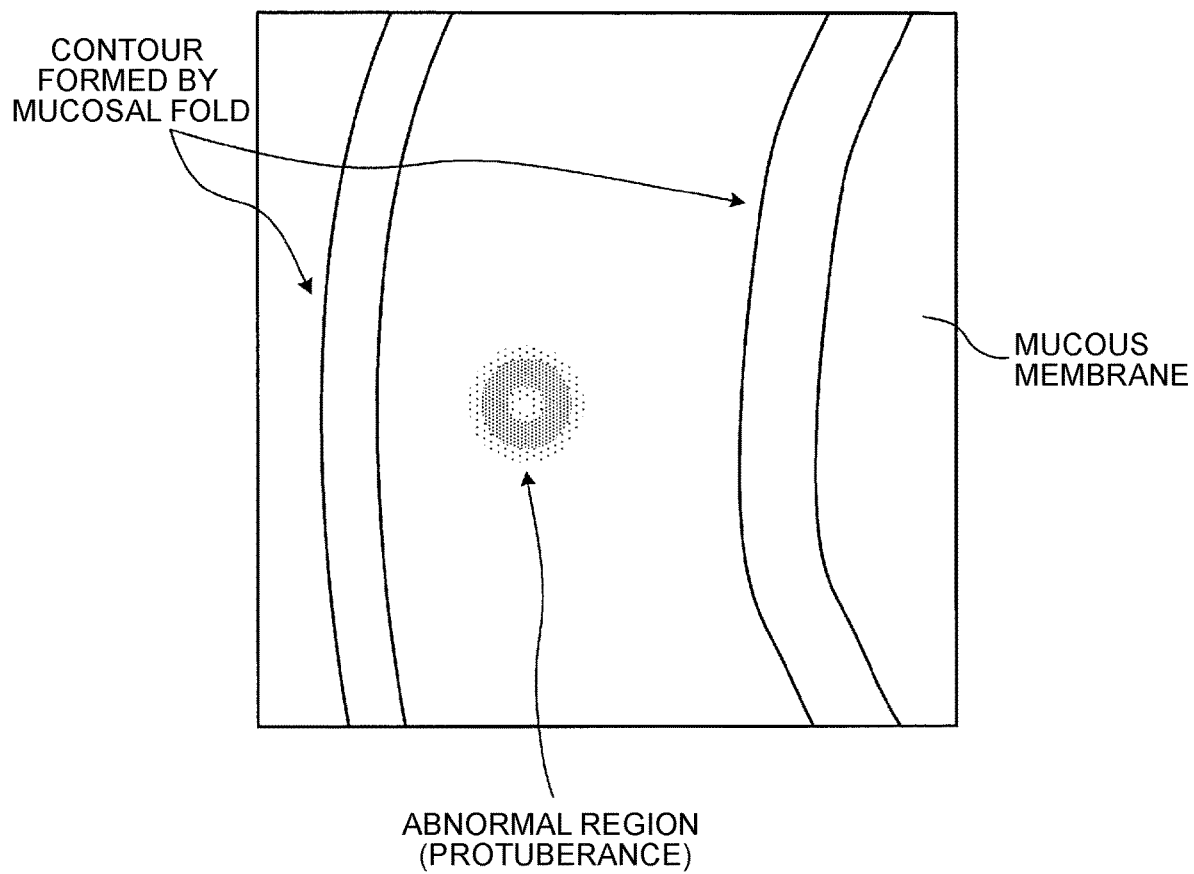
FIG. 2 is a second exemplary diagram for describing a second situation of the present disclosure.

FIGS. 1 and 2 are respective first and second exemplary diagrams for describing the respective first and second situations in which the present disclosure is defined. In detail, FIGS. 1 and 2 are each a diagram schematically illustrating an image (intraductal image) of a living body captured by an endoscope introduced into the living body to observe the living body. Although is not shown in the drawings, but as one of ordinary skill in the art would appreciate that the endoscope or the likes is used to examine the interior of a hollow organ or cavity of the living body.

The endoscope often captures the image of the mucosal surface of the ductal inner wall in the living body obliquely. Thus, the intraductal image captured by the endoscope shows the mucosal surface on the near side of the duct at a short imaging distance to the mucosal surface of a ductal deep portion at a long imaging distance, and may show an abnormal region that is likely to have a lesion, as illustrated in FIG. 1.

Alternatively, the endoscope may capture the image of the mucosal surface of the ductal inner wall in the living body from the front, as illustrated in FIG. 2. In the case of capturing the image of the mucosal surface from the front, no ductal deep portion is shown in the image, and the abnormal region is shown differently from the obliquely captured image.

Other images captured by the endoscope may differ in the imaging distance to the mucosal surface of the ductal inner wall in the living body, and may be defocused or have motion blur.

An image processing device according to an embodiment of the disclosure analyzes the aforementioned differences in the imaging situation, and adaptively detects a specific region including an abnormal region. The specific region noted herein is defined as a region in which the property or state of the subject in the intraductal image satisfies a predetermined condition. For example, in the case where the intraductal image is an intraductal image of a living body (intravital luminal image), the specific region is such a region where the tissue property of the living body or the state in the living body satisfies a predetermined condition. Generally, examples of the specific region include abnormal regions such as a region where the tissue property of the living body has changed, for example, aphtha, ulcer, erosion, polyp, tumor, redness, or chorionic abnormality, and a region where the state in the living body has changed, for example, bleeding. The specific region may be a region of a part of the image, or a region of the entire image. Each image captured by the endoscope is assumed to be a color image having pixel values corresponding to the wavelength components of R (red), G (green), and B (blue) at each pixel position, though the present disclosure is not limited to such arrangements. An operation of the first embodiment will now be described with reference to the drawings.

Figure 3:
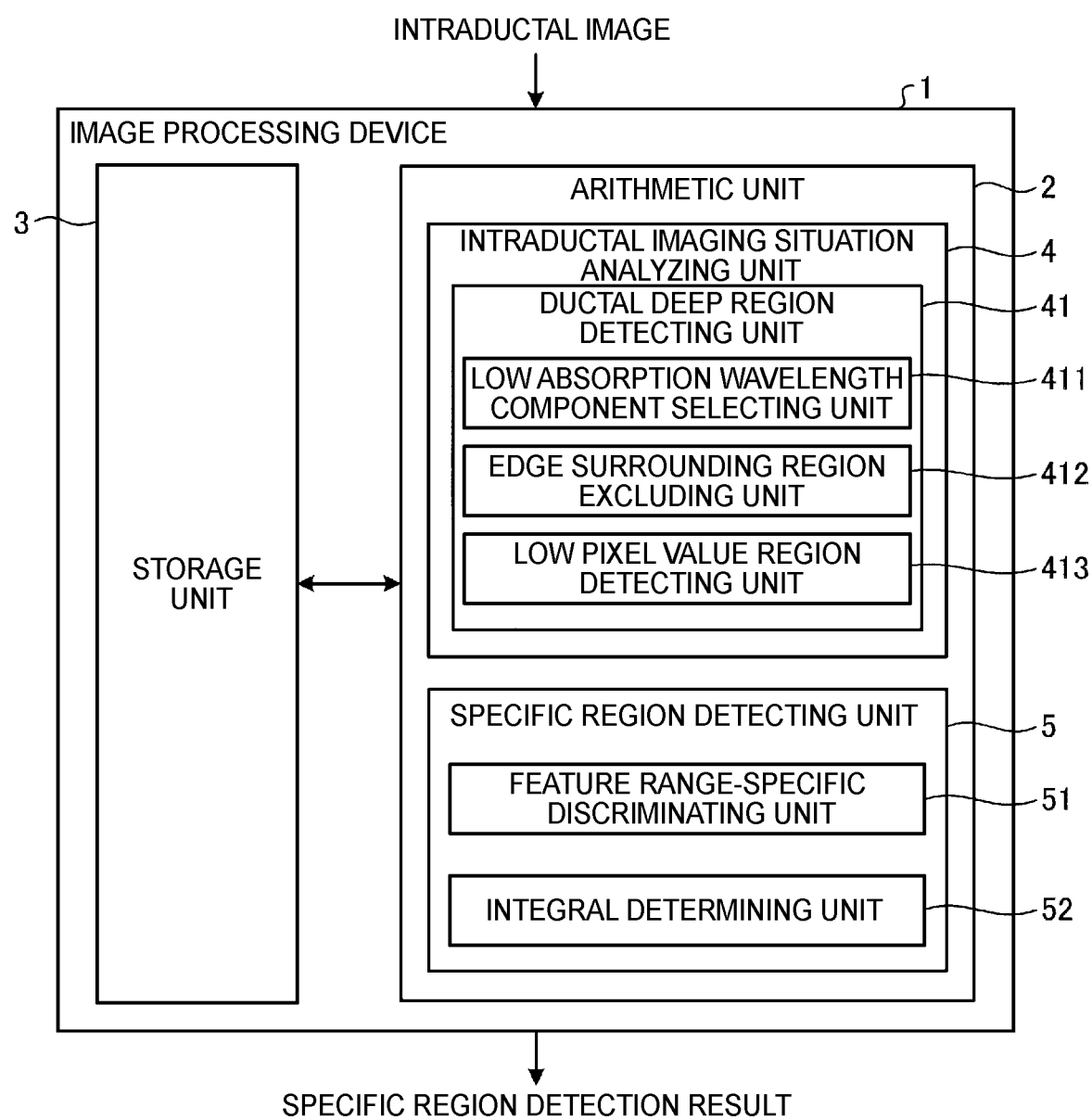
FIG. 3 is a block diagram illustrating the functional structure of an image processing device according to a first Embodiment.

FIG. 3 is a block diagram illustrating the functional structure of an image processing device according to the first Embodiment. An image processing device 1 illustrated in FIG. 3 includes an arithmetic unit 2 and a storage unit 3.

The arithmetic unit 2 includes an intraductal imaging situation analyzing unit 4 that can analyze, an intraductal image. The intraductal imaging situation is determined based on the relationship between the subject and the part that captures the image of the subject, and a specific region detecting unit 5 that can detect a specific region depending on the intraductal imaging situation.

The intraductal imaging situation analyzing unit 4 includes a ductal deep region detecting unit 41 that can detect a ductal deep region in the intraductal image. The ductal deep region detecting unit 41 includes a low absorption wavelength component selecting unit 411 that can select a low absorption wavelength component with the lowest degree of absorption and scattering in the living body. An edge surrounding region excluding unit 412 excludes the pixels of an edge surrounding region in the intraductal image of the low absorption wavelength component. Finally, a low pixel value region detecting unit 413 that detects a region not greater than a predetermined threshold in the image of the low absorption wavelength component from which the pixels of the edge surrounding region have been excluded.

Typically, the region where the pixels detected by the low pixel value region detecting unit 413 exists together can be understood to be the ductal deep region. The ductal deep region detecting unit 41 performs the labeling processing (the general labeling processing theory is described in the Reference Labeling, "Digital Image Processing" p. 181, CG-ARTS Society) on the pixels detected by the low pixel value region detecting unit 413 to combine the connecting pixels as one region, and then detects, from among the regions whose areas are not less than a predetermined threshold, the largest region as the ductal deep region. In the case where there is no region whose area is not less than the predetermined threshold, the ductal deep region detecting unit 41 can determine that there is no ductal deep region.

The low absorption wavelength component selecting unit 411 selects, for example in the case where the image is composed of R, G, and B components, the R component which is away from the blood absorption band, is long-wavelength, and is unlikely to be affected by absorption and scattering in the living body. As a result of such selection by the low absorption wavelength component selecting unit 411, a decrease in pixel value due to blood vessels and the like shown on the mucosal surface can be prevented to obtain pixel value information that correlates most closely with the imaging distance to the mucosal surface.

Continue referring to FIG. 3, the edge surrounding region excluding unit 412 specifies an edge region by, for example, edge extraction processing (the general edge extraction processing theory is described in the Reference: Edge Extraction (p. 114) and Contour Detection (p. 209), "Digital Image Processing," CG-ARTS Society), and performs expansion processing (the general expansion processing theory is described in the Reference: Contraction and Expansion Processing, "Digital Image Processing" p. 179, CG-ARTS Society) on the edge region to specify its surrounding region, and excludes the surrounding region. As a result of the edge surrounding region excluding unit 412 excluding the edge surrounding region, any region that has a possibility of being erroneously detected as the mucous membrane of the ductal deep portion, such as a shaded portion appearing around a contour edge by a mucosal fold, can be excluded. The mucous membrane herein is where the pixel value of the low absorption wavelength component decreases as illumination light is hard to reach.

The low pixel value region detecting unit 413 detects each pixel whose pixel value is not greater than the predetermined threshold, in the image of the low absorption wavelength component from which the edge surrounding region has been excluded. The low pixel value region detecting unit 413 may detect, in the intraductal image of the low absorption wavelength component from which the edge surrounding region has been excluded, each pixel whose pixel value is not greater than a threshold set based on a pixel value range for the pixels in the intraductal image.

The specific region detecting unit 5 includes a feature range-specific discriminating unit 51 that can calculate a plurality of specific region discrimination indices based on feature values calculated from a plurality of regions different in range. An integral determining unit 52 then detects the specific region by integral determination on the specific region discrimination indices depending on the intraductal imaging situation.

The feature range-specific discriminating unit 51 first sets a plurality of feature value calculation regions from small to large ranges, at any position in the image. A plurality of feature value calculation regions that have the same center position but differ in range can be set, as well. The feature range-specific discriminating unit 51 calculates feature values from each region. Various feature values, such as color, contour (edge), pixel value surface shape (pixel value gradient), and texture, are available. A plurality of feature values calculated from one feature value calculation region can be combined as a feature vector. The same number of feature vectors as the set feature value calculation regions can be thus generated.

Next, the feature range-specific discriminating unit 51 calculates a specific region discrimination index based on each feature vector. Various methods of calculating a specific region discrimination index based on a feature vector are known. For example, with a typical statistical discrimination method, specific region discrimination index P(x) of whether or not feature vector x satisfies a specific condition can be calculated based on a probability model expressed by the following Formula (1):

$$P(x) = \frac{1}{(2\pi)^{k/2} \times |Z|^{1/2}} \exp\left\{(x-\mu)^t \times \left(-\frac{1}{2}\right) Z^{-1} \times (x-\mu)\right\} \quad (1)$$

In the right side of Formula (1), k is the number of dimensions of the feature vector, x is the feature vector (k×1 matrix) of the inspection region to be discriminated, p is the mean vector (k×1 matrix) of the feature vectors in (a plurality of) samples of the specific region, Z is the variance-covariance matrix (k×k matrix) of the feature vectors in (a plurality of) samples of the specific region, |Z| is the determinant of Z, and $Z^{-1}$ is the inverse matrix of Z.

Although the specific region discrimination index calculation method using the probability model is described as an example herein, any method capable of calculating the specific region discrimination index may be used. For example, the specific region discrimination index may be calculated using a method based on the feature spatial distance to a representative feature vector or a method based on the distance to a discrimination boundary in the feature space.

The integral determining unit 52 performs the following process within the operation of the image processing device 52. In the case where the ductal deep region is in the image, the image of the ductal inner wall is captured obliquely, and so the accuracy of specific region detection based on global information using the entire ductal structure is expected to be high. In such a case, the integral determining unit 52 performs determination while attaching or assigning a value of importance to the specific region discrimination index that is based on the feature value of a large feature value calculation region. Specifically, the integral determining unit 52 multiplies each of the plurality of specific region discrimination indices by a weight corresponding to the level of importance, and adds the resulting specific region discrimination indices together, thus calculating a final determination index. In the case where this value is not less than a threshold, the integral determining unit 52 detects the specific region. Thus, attaching or assigning importance to a specific region discrimination index means to assign a larger weight to the specific region discrimination index than other specific region discrimination indices in the calculation.

In the case where there is no deep region in the image, the image of the ductal inner wall is captured from the front, and therefore, the specific region detection based on global information using the entire ductal structure is not adequate. However, in the case where the range of the region used for feature value calculation is large, there is a possibility of a decrease in detection accuracy caused by the inclusion of such a region (e.g., specular reflection, residue, bubble, normal fold, etc.) that leads to lower accuracy. In such a case, the integral determining unit 52 can perform integral determination while attaching importance to the specific region discrimination index that is based on the feature value of a small feature value calculation range (i.e., local information).

Still referring to FIG. 3, the arithmetic unit 2 is realized using a general-purpose processor such as a central processing unit (CPU) or a special-purpose processor of any type of arithmetic circuitry for executing specific functions such as an application specific integrated circuit (a.k.a, ASIC). In the case where the arithmetic unit 2 is a general-purpose processor, the arithmetic unit 2 reads various programs stored in the storage unit 3 to issue instructions, transfer data, and etc. to the structural elements of the image processing device 1, thus exercising centralized control on the overall operation of the image processing device 1. In the case where the arithmetic unit 2 is a special-purpose processor, the processor may execute various processes by itself, or the processor and the storage unit 3 may execute various processes coordinately or integrally by using various data, and etc. stored in the storage unit 3. The arithmetic unit in each of the embodiments and modifications described hereinafter is realized in the same way as the arithmetic unit 2.

The storage unit 3 is realized using any of various types of integrated circuit (IC) memory such as read only memory (ROM) or random access memory (RAM), a hard disk included in the image processing device or connected via a data communication terminal, an information recording device such as CD-ROM and its reader, or the like. The storage unit 3 stores not only image data of intraductal images acquired by the image processing device 1, but also programs for operating the image processing device 1 and causing the image processing device 1 to execute various functions and data used in the execution of the programs. specifically, the storage unit 3 stores an information processing program according to the first Embodiment, and various parameters such as thresholds used in the image processing. The storage unit in each of the embodiments described hereinafter is realized in the same way as the storage unit 3.

Various programs such as the image processing program stored in the storage unit 3 may be recorded in a computer-readable recording medium. The recording of various programs in the storage unit 3 or the recording medium may be performed when shipping the computer or the recording medium as a product, or performed by download via a communication network. The communication network mentioned herein can be realized by, for example, an existing public line network, a local area network (LAN), or a wide area network (WAN), and may be wired or wireless.

The image processing device 1 having the structure described hereinabove may be realized using one computer or a plurality of computers. In the case of multiple computers, the computers may perform processes in conjunction with each other while transmitting and receiving data via a communication network. The computer (or computers) mentioned herein may be, for example, a general-purpose personal computer or a server. The same applies to the image processing device in each of the embodiments and modifications described hereinbefore or hereinafter.

The operation of the image processing device 1 described hereinabove may be included in a processor that constitutes part of an endoscopic system introduced into a test object to observe the inside of the test object and controls the entire endoscopic system. The same applies to the image processing device in each of the embodiments and modifications described hereinbefore or hereinafter.

Figure 4:
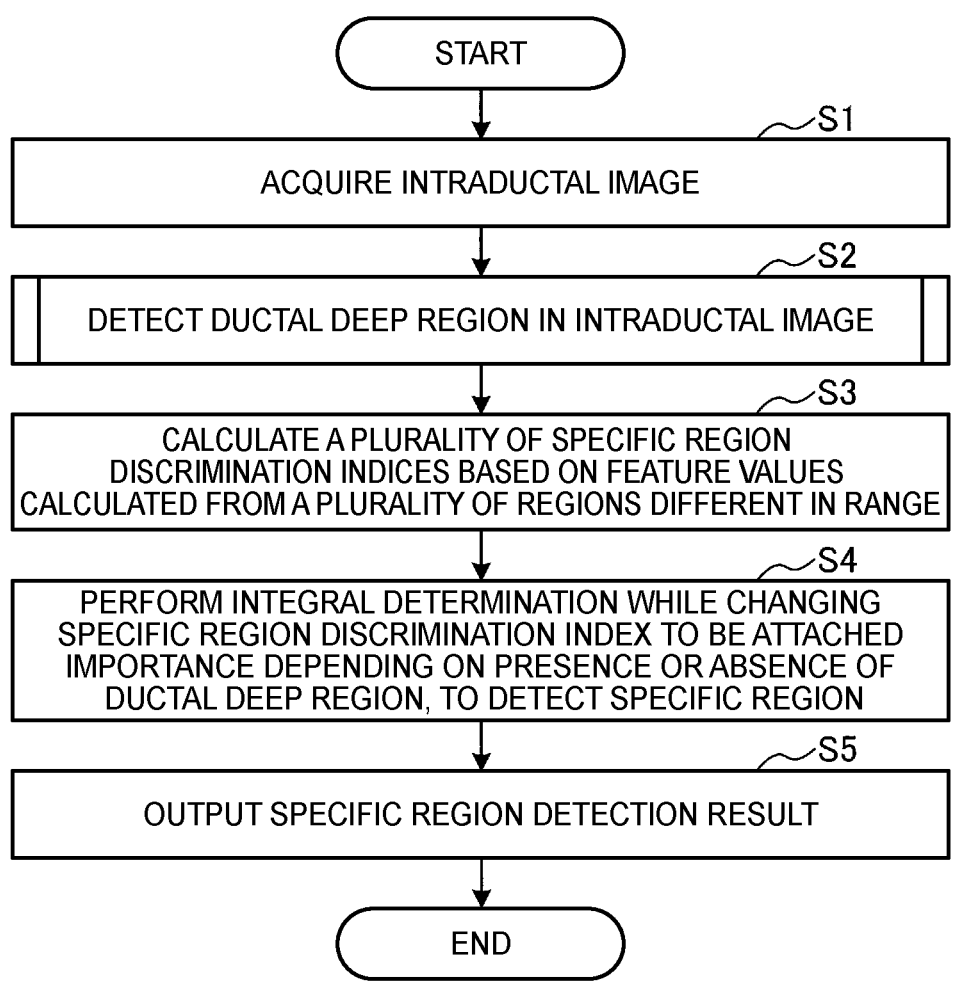
FIG. 4 is a flowchart illustrating the process performed by the image processing device according to the first Embodiment.

Now referring to FIG. 4, which is a flowchart illustrating the process performed by the image processing device 1. First, the arithmetic unit 2 acquires the intraductal image to be processed as depicted in step S1.

In step S2, the ductal deep region detecting unit 41 detects the ductal deep region in the intraductal image.

Figure 5:
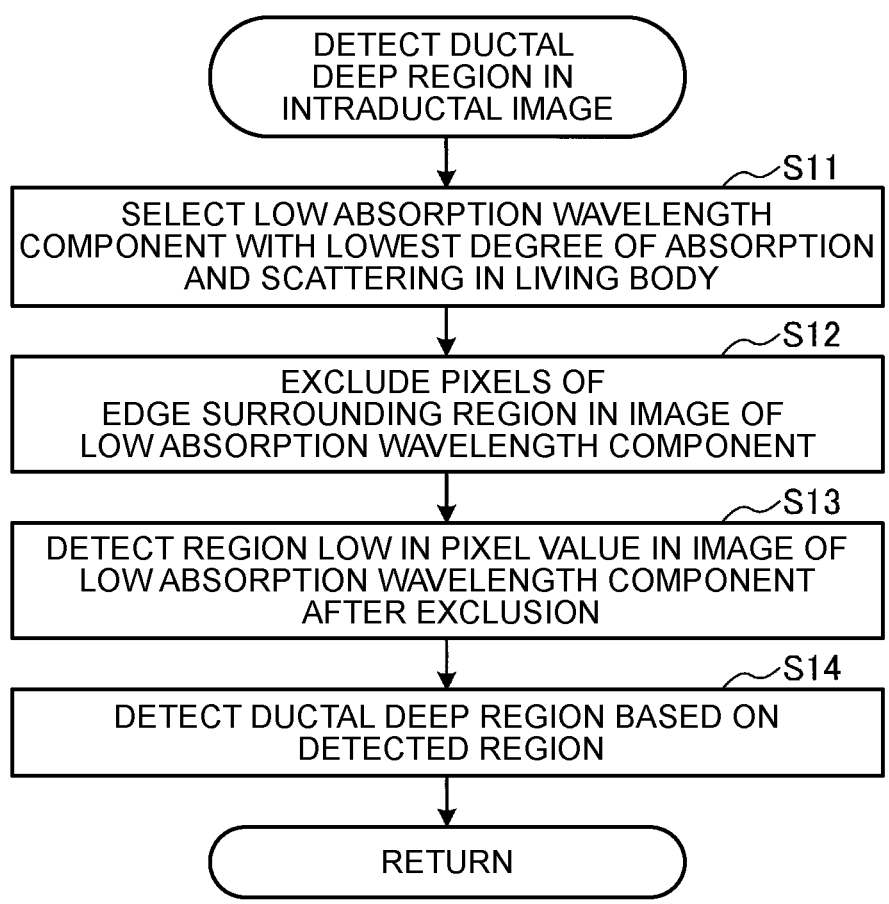
FIG. 5 is a flowchart illustrating the process performed by a ductal deep region detecting unit in the image processing device according to the first Embodiment.

FIG. 5 is a flowchart illustrating the process performed by the ductal deep region detecting unit 41. The process by the ductal deep region detecting unit 41 is described herein below, with reference to FIG. 5. In step S11, the low absorption wavelength component selecting unit 411 selects the low absorption wavelength component with the lowest degree of absorption and scattering in the living body. For example, in the case where the image is composed of R, G, and B components, the low absorption wavelength component selecting unit 411 can select the R component as mentioned hereinabove.

Next in step S12, the edge surrounding region excluding unit 412 excludes the pixels of the edge surrounding region in the intraductal image of the low absorption wavelength component. This prevents the edge surrounding region from being erroneously detected as the ductal deep region.

Next in step S13, the low pixel value region detecting unit 413 detects each region low in pixel value, i.e. each region of pixels whose pixel values are not greater than the predetermined threshold, in the image of the low absorption wavelength component from which the edge surrounding region has been excluded. Since the ductal deep portion is at a long imaging distance, the pixel value of the image of the low absorption wavelength component is low in the ductal deep portion, as discussed hereinabove.

Finally, in step S14, the ductal deep region detecting unit 41 detects the ductal deep region by known labeling processing or the like, based on the region detected by the low pixel value region detecting unit 413. This completes the ductal deep region detection process by the ductal deep region detecting unit 41 as discussed in step S2.

Although the first Embodiment describes the method of detecting the ductal deep region based on the pixel value which correlates with the imaging distance, this is merely an example. For instance, the ductal deep region may be detected based on the method described in Japanese Patent Application No. 2003-93328.

Moreover, processes such as correcting pixel value inconsistency caused by an optical system or an illumination system or excluding non-mucosal regions which include specular reflection, residue, and bubble may be performed before the ductal deep region detection process. Lower accuracy of the subsequent processes can be prevented in this manner.

In step S3 which follows step S2, the feature range-specific discriminating unit 51 calculates the plurality of specific region discrimination indices based on the feature values calculated from the plurality of regions different in range. For example, the feature range-specific discriminating unit 51 can calculate specific region discrimination index P(x) based on the probability model defined in the foregoing Formula (1) hereinabove.

Next in step 4, the integral determining unit 52 performs integral determination while changing the specific region discrimination index to be attached or assigned importance depending on the presence or absence of the ductal deep region, to detect the specific region.

In final step S5, the arithmetic unit 2 outputs the specific region detection result. The image processing device 1 thus completes the series of processes. The ductal deep region detection process in step S2 and the specific region discrimination index calculation process in step S3 may be performed in reverse order or concurrently.

According to the first Embodiment described hereinabove, the plurality of specific region discrimination indices of different feature value calculation ranges can be integrally determined depending on the presence or absence of the ductal deep region. Given that the image varies due to the difference in imaging direction (e.g., oblique, front, and the likes) to the ductal inner wall, the specific region can be detected accurately by attaching or assigning importance to the specific region discrimination index that is based on the more effective feature value.

Figure 6:
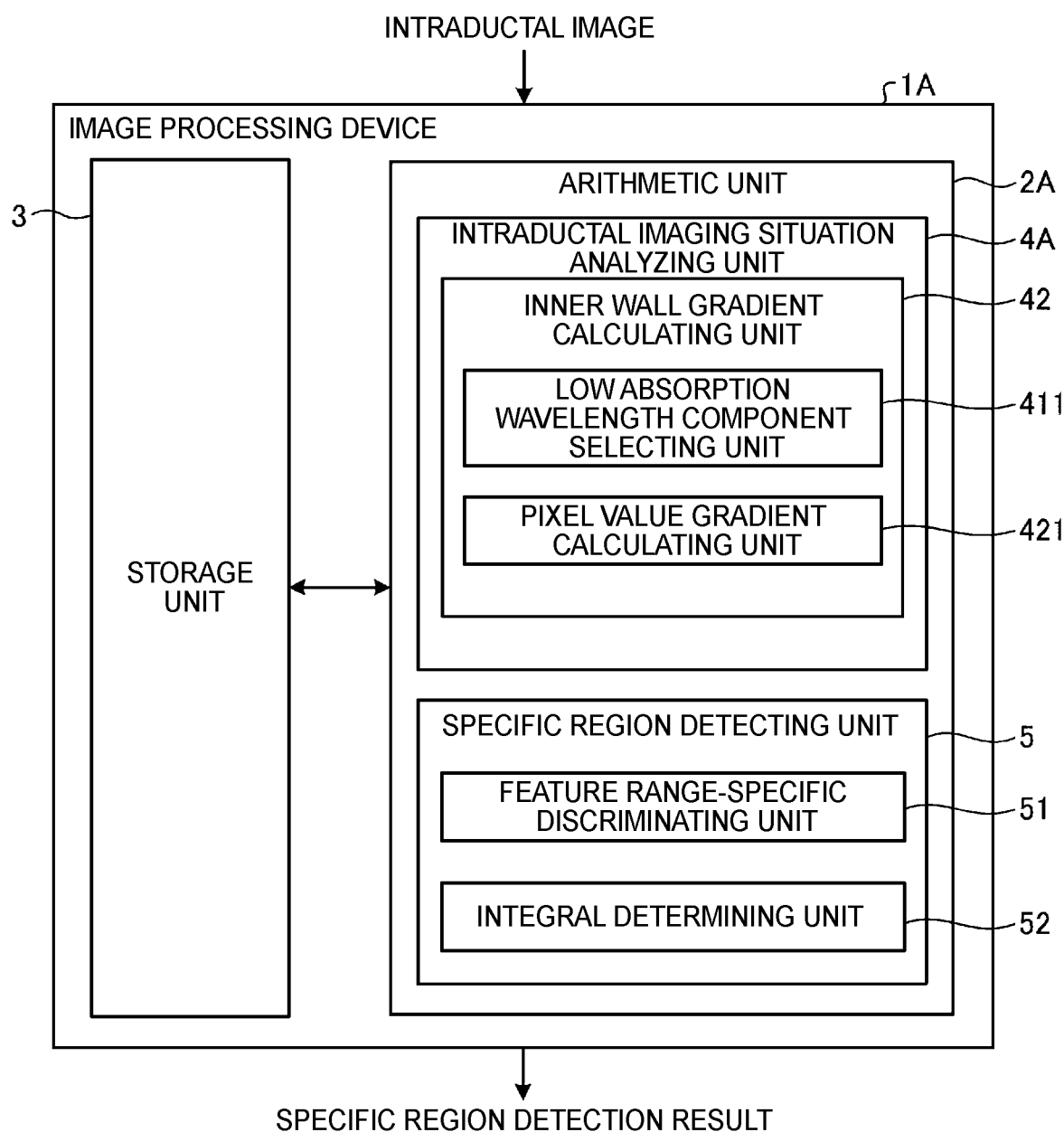
FIG. 6 is a block diagram illustrating the functional structure of an image processing device according to Modification 1-1 of the first Embodiment.

FIG. 6 is a block diagram illustrating the functional structure of an image processing device according to Modification 1-1 of the first Embodiment. In an image processing device 1A illustrated in FIG. 6, the structural elements having the same functions as those in the image processing device 1 illustrated in FIG. 3 are given the same reference signs as in FIG. 3.

The image processing device 1A includes an arithmetic unit 2A and the storage unit 3. The arithmetic unit 2A includes an intraductal imaging situation analyzing unit 4A and the specific region detecting unit 5.

The intraductal imaging situation analyzing unit 4A includes an inner wall gradient calculating unit 42 that calculates the gradient (e.g., inner wall gradient) of the ductal inner wall in the intraductal image. The inner wall gradient calculating unit 42 includes the low absorption wavelength component selecting unit 411 that selects the low absorption wavelength component with the lowest degree of absorption and scattering in the living body, and a pixel value gradient calculating unit 421 that calculates the pixel value gradient of the low absorption wavelength component.

The pixel value gradient calculating unit 421 calculates the magnitude and direction of the pixel value gradient, based on primary differential filter output ΔX in the X direction of a predetermined size and primary differential filter output ΔY in the Y direction of the same size (the general theory of Differential Filter is described in Reference: Differential Filter, "Digital Image Processing," p. 115, CG-ARTS Society). The pixel value gradient calculating unit 421 may calculate the gradient of the ductal inner wall at each pixel position or at predetermined sampling intervals.

The integral determining unit 52 in the specific region detecting unit 5 performs integral determination while changing the specific region discrimination index to be attached importance depending on the magnitude of the inner wall gradient, so as to detect the specific region. In the case where the average magnitude of the inner wall gradients calculated in a plurality of locations is not less than a predetermined threshold, the image of the ductal inner wall is captured obliquely, and so the accuracy of specific region detection based on global information using the entire ductal structure is expected to be high. In such a case, the integral determining unit 52 performs determination while attaching or assigning importance to the specific region discrimination index that is based on the feature value of a large feature value calculation range.

In the case where the average magnitude of the inner wall gradients is less than the predetermined threshold, the image of the ductal inner wall is captured from the front, and so there is a possibility that the detection accuracy decreases if the range of the region used for feature value calculation is large. In such a case, the integral determining unit 52 performs determination while attaching importance to the specific region discrimination index that is based on the feature value of a small feature value calculation range.

Figure 7:
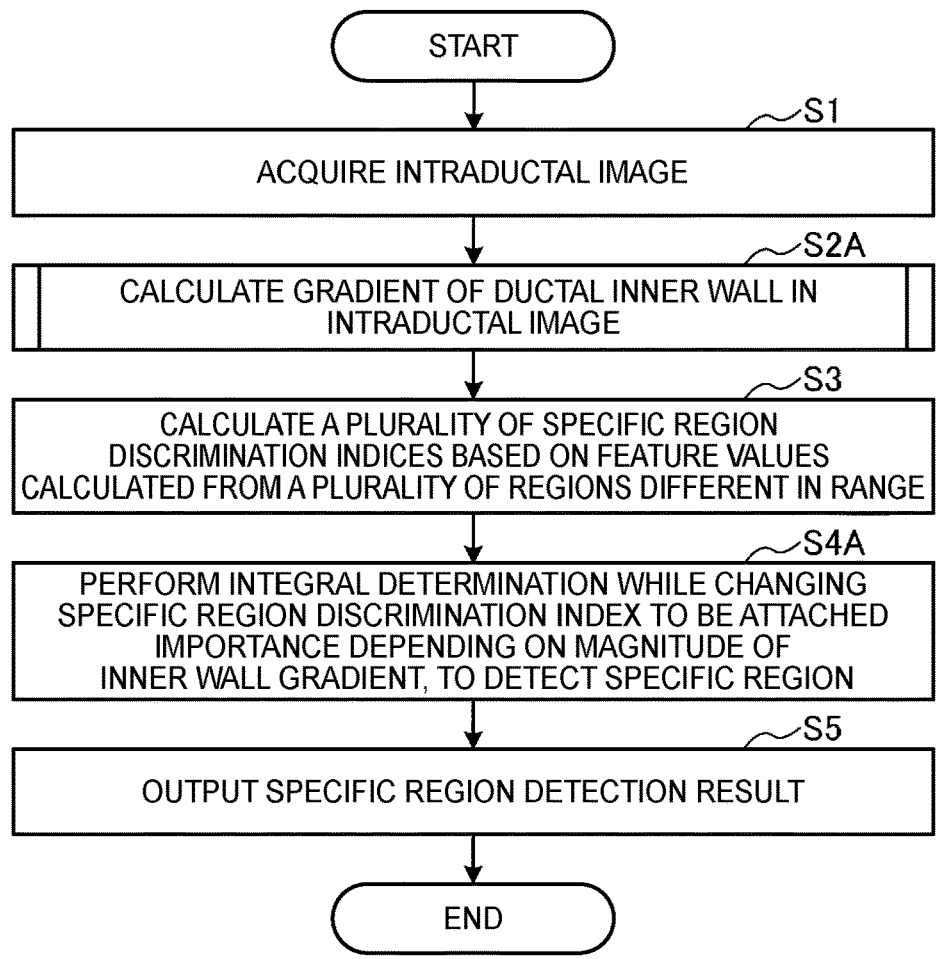
FIG. 7 is a flowchart illustrating the process performed by the image processing device according to Modification 1-1 of the first Embodiment.

FIG. 7 is a flowchart illustrating the process performed by the image processing device 1A. In FIG. 7, the same processes as those in the flowchart illustrated in FIG. 4 are given the same step numbers. The following describes the processes after step S1.

In step S2A, the inner wall gradient calculating unit 42 calculates the gradient of the ductal inner wall in the intraductal image (step S2A).

Figure 8:
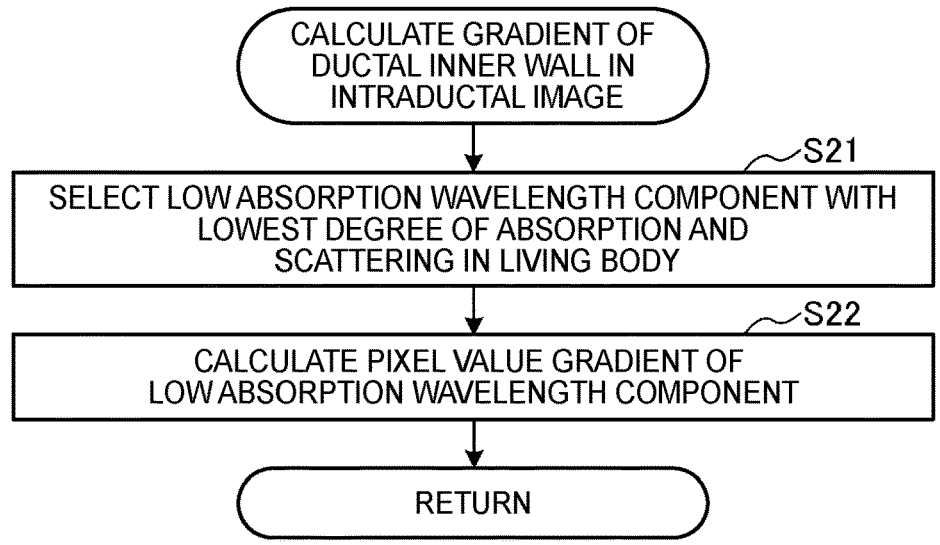
FIG. 8 is a flowchart illustrating the process performed by an inner wall gradient calculating unit in the image processing device according to Modification 1-1 of the first Embodiment.

FIG. 8 is a flowchart illustrating the process performed by the inner wall gradient calculating unit 42. The process by the inner wall gradient calculating unit 42 is described below, with reference to FIG. 8. In step S21, the low absorption wavelength component selecting unit 411 selects the low absorption wavelength component with the lowest degree of absorption and scattering in the living body.

Next in step S22, the pixel value gradient calculating unit 421 calculates the pixel value gradient of the selected low absorption wavelength component. This completes the ductal inner wall gradient calculation process in the intraductal image by the inner wall gradient calculating unit 42 of the step S2A.

In step S3 which follows step S2A, the feature range-specific discriminating unit 51 calculates the plurality of specific region discrimination indices based on the feature values calculated from the plurality of regions different in range.

Next in step S4A, the integral determining unit 52 performs integral determination while changing the specific region discrimination index to be attached importance depending on the magnitude of the inner wall gradient, to detect the specific region.

Lastly, in step S5, the arithmetic unit 2A outputs the specific region detection result step S5. The image processing device 1A thus completes the series of processes. The inner wall gradient calculation process in step S2A and the specific region discrimination index calculation process in step S3 may be performed in reverse order or concurrently.

According to Modification 1-1 of the first Embodiment described hereinabove, the plurality of specific region discrimination indices of different feature value calculation ranges can be integrally determined depending on the magnitude of the inner wall gradient. Given that the image varies due to the difference in imaging direction (oblique, front, and the likes) to the ductal inner wall, the specific region can be detected accurately by attaching importance to the specific region discrimination index that is based on the more effective feature value.

In Modification 1-1, the intraductal imaging situation analyzing unit 4A may further include the ductal deep region detecting unit 41 described in the first Embodiment. In this case, the integral determining unit 52 performs integral determination depending on the presence or absence of the ductal deep region and the magnitude of the inner wall gradient.

Figure 9:
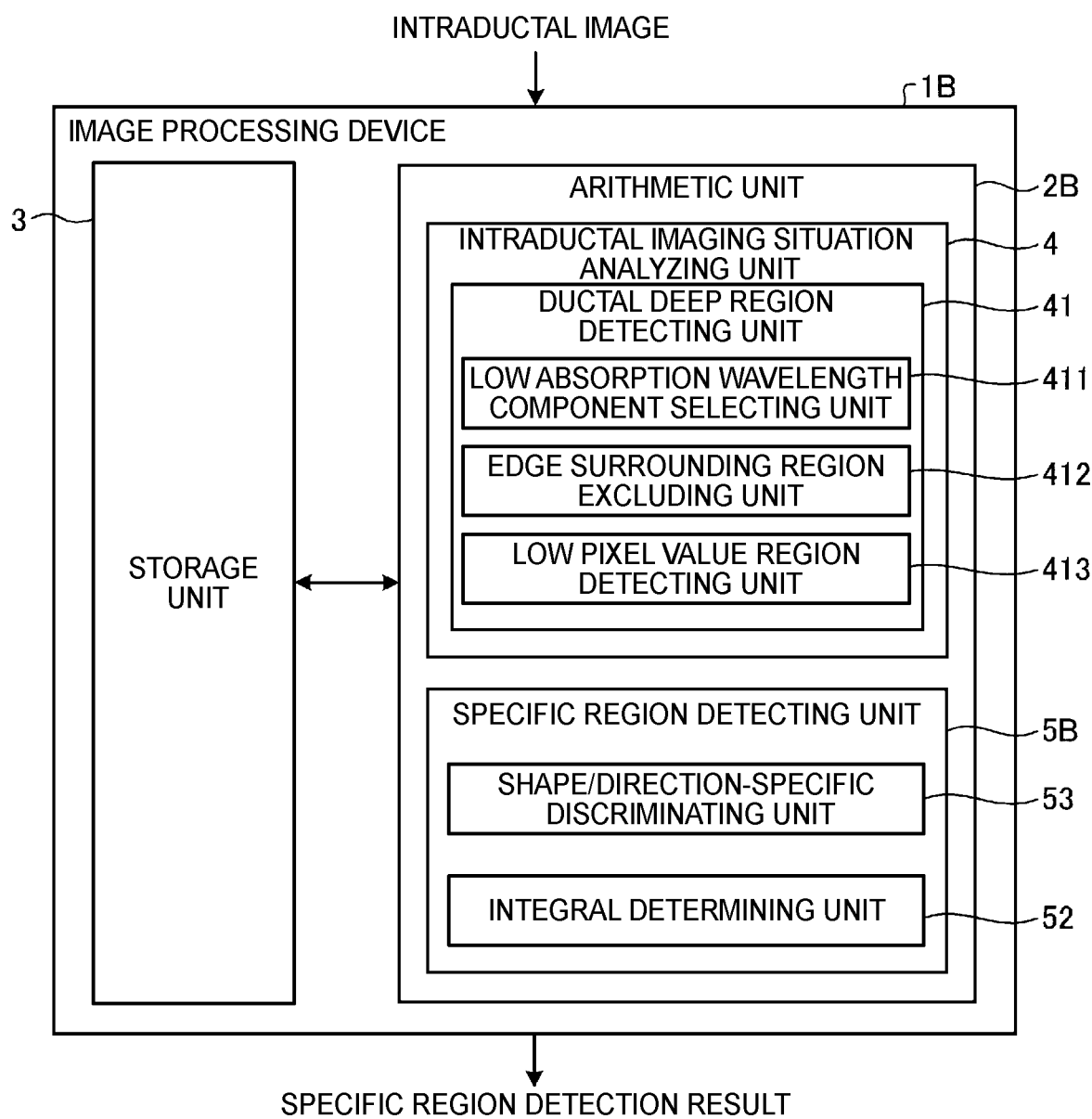
FIG. 9 is a block diagram illustrating the functional structure of an image processing device according to Modification 1-2 of the first Embodiment.

FIG. 9 is a block diagram illustrating the functional structure of an image processing device according to Modification 1-2 of the first Embodiment. In an image processing device 1B illustrated in FIG. 9, the structural elements having the same functions as those in the image processing device 1 illustrated in FIG. 3 are given the same reference signs as in FIG. 3.

The image processing device 1B includes an arithmetic unit 2B and the storage unit 3. The arithmetic unit 2B includes the intraductal imaging situation analyzing unit 4 and a specific region detecting unit 5B.

The specific region detecting unit 5B includes a shape/direction-specific discriminating unit 53 that calculates a plurality of specific region discrimination indices based on feature values calculated from a plurality of regions different in shape and/or direction, and the integral determining unit 52.

Figure 10:
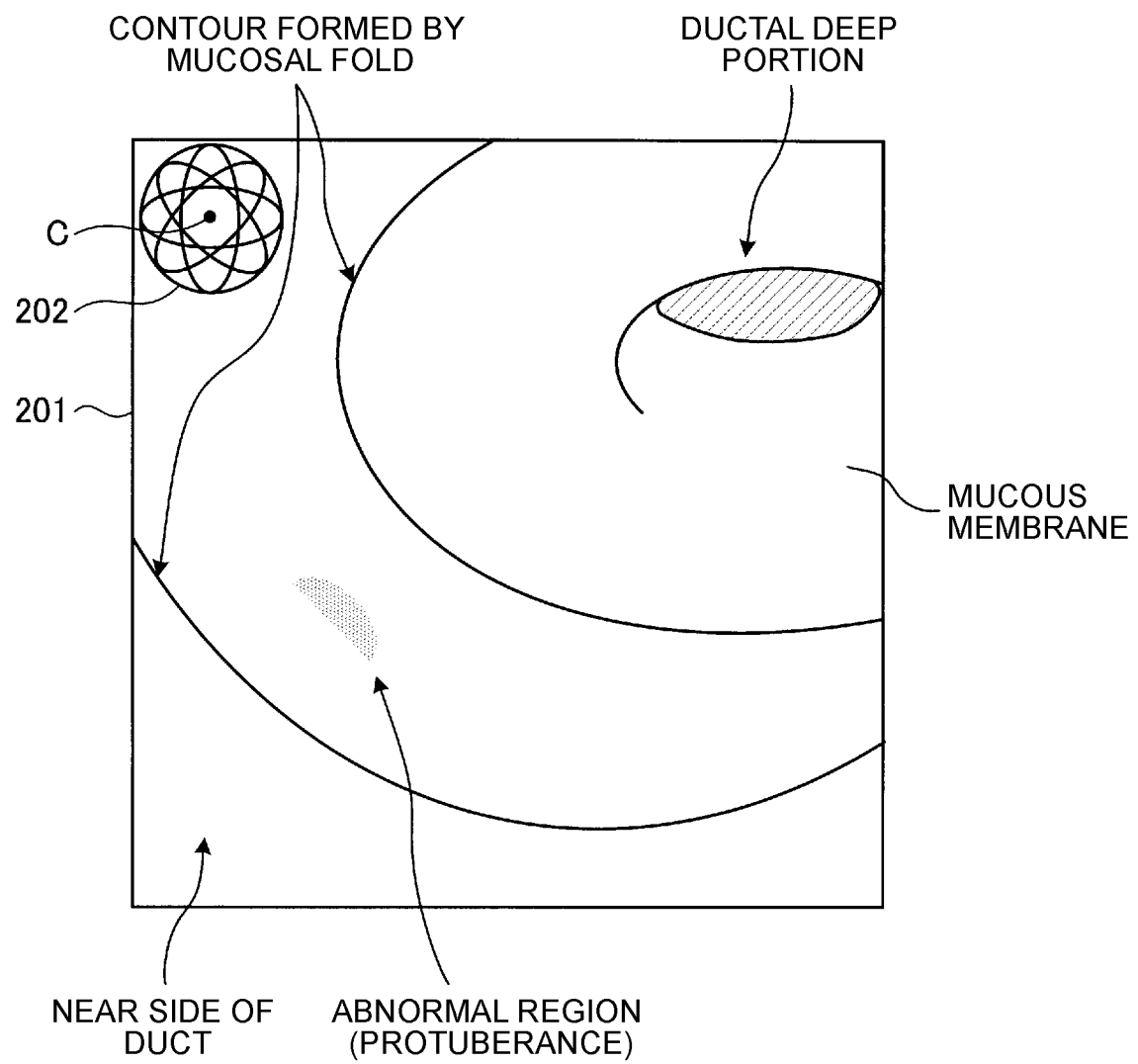
FIG. 10 is a diagram schematically illustrating an example of setting feature value calculation regions by a shape/direction-specific discriminating unit in the image processing device according to Modification 1-2 of the first Embodiment.

FIG. 10 is a diagram schematically illustrating an example of setting feature value calculation regions by the shape/direction-specific discriminating unit 53. As illustrated in FIG. 10, the shape/direction-specific discriminating unit 53 sets a feature value calculation region group 202 made up of a plurality of elliptic regions (e.g., four elliptic regions in FIG. 10) that differ in circular region and major axis direction, with any position C in an intraductal image 201 as the center. The shape/direction-specific discriminating unit 53 may set a plurality of feature value calculation region groups 202 while scanning the intraductal image 201 for the center position of the feature value calculation region group 202 according to a predetermined rule, or set a plurality of feature value calculation region groups 202 different in center position concurrently. The shape of each region in the feature value calculation region group is not limited to that illustrated in FIG. 10. For example, the shape/direction-specific discriminating unit 53 may set a circular region, and then scan the intraductal image 201 while rotating the circular region to set a plurality of feature value calculation regions.

The integral determining unit 52 performs integral determination while changing the specific region discrimination index to be attached importance depending on the direction of the deep region, to detect the specific region. In the case where the ductal deep region is in the image, the image of the ductal inner wall is captured obliquely, and the abnormal region tends to appear as an image that is shorter in the direction of the deep region (depth direction) and longer in the direction orthogonal to the direction of the deep region as illustrated in FIG. 1. Therefore, the accuracy of specific region detection based on the feature value calculated from a region of a similar shape is expected to be high. In such a case, the integral determining unit 52 performs determination while attaching or assigning importance to the specific region discrimination index that is based on the feature value calculated from a region longer in the direction orthogonal to the direction of the deep region.

In the case where the ductal deep region is not in the image, the image of the ductal inner wall is captured from the front, where the aforementioned change in image length does not occur (see FIG. 2). In such a case, the integral determining unit 52 performs determination while attaching importance to the specific region discrimination index that is based on the feature value calculated from a circular region not dependent on the direction.

In the oblique imaging situation, the image also changes in the rotation direction depending on the vertical position of the part capturing the image. In this case, the integral determining unit 52 may perform determination while attaching importance to the specific region discrimination index that is based on the feature value calculated from a region in a direction according to the direction of the ductal deep region.

Figure 11:
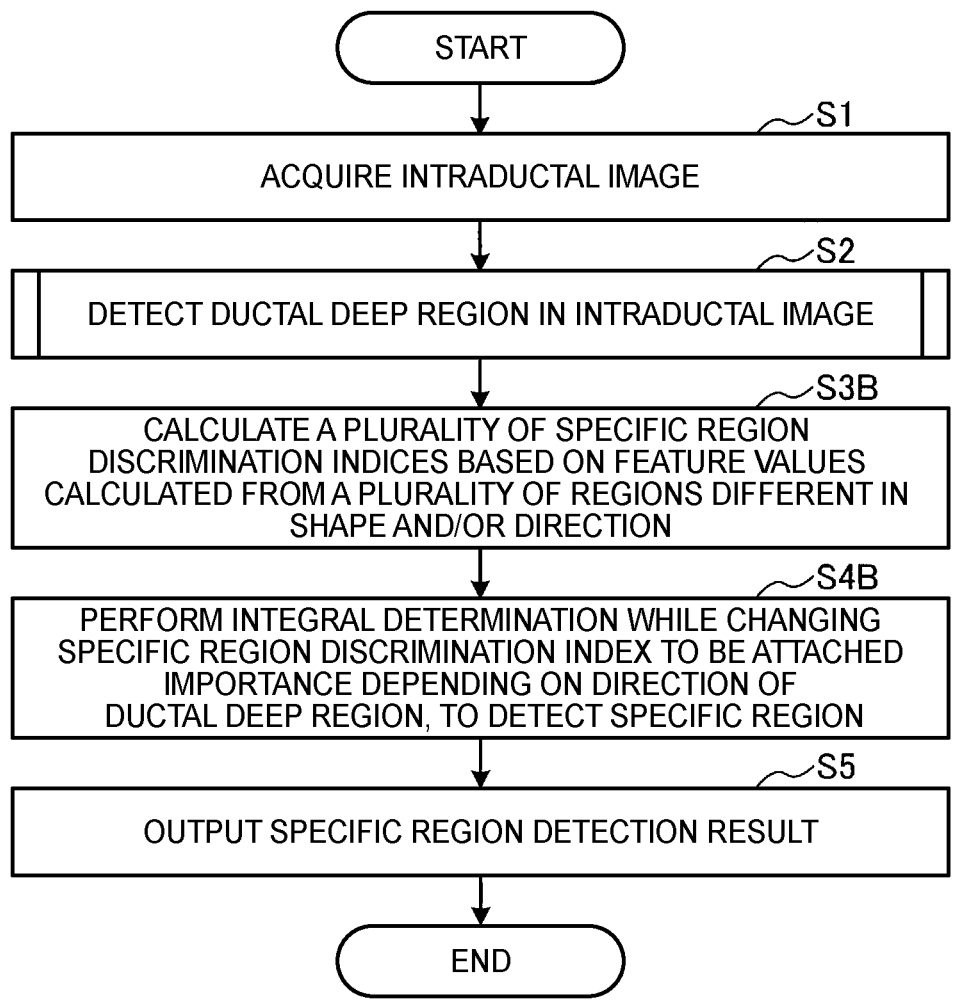
FIG. 11 is a flowchart illustrating the process performed by the image processing device according to Modification 1-2 of the first Embodiment.

FIG. 11 is a flowchart illustrating the process performed by the image processing device 1B. In FIG. 11, the same processes as those in the flowchart illustrated in FIG. 4 are given the same step numbers. The following describes the processes after the step S2.

In step S3B, the shape/direction-specific discriminating unit 53 calculates the plurality of specific region discrimination indices based on the feature values calculated from the plurality of regions different in shape and/or direction. For example, the shape/direction-specific discriminating unit 53 calculates the feature values from the plurality of feature value calculation regions using the feature value calculation region group 202 illustrated in FIG. 10.

Next in step S4B, the integral determining unit 52 performs integral determination while changing the specific region discrimination index to be attached importance depending on the direction of the ductal deep region, to detect the specific region.

Finally, in step S5, the arithmetic unit 2B outputs the specific region detection result. The image processing device 1B thus completes the series of processes. The ductal deep region detection process in step S2 and the specific region discrimination index calculation process in step S3B may be performed in reverse order or concurrently.

According to Modification 1-2 described hereinabove, the plurality of specific region discrimination indices of the feature value calculation regions different in shape and/or direction can be integrally determined depending on the direction of the ductal deep region. Given that the image varies due to the difference in imaging direction to the ductal inner wall, the specific region can be detected accurately by attaching importance to the specific region discrimination index that is based on the more effective feature value.

In Modification 1-2, the image processing device 1B may include the intraductal imaging situation analyzing unit 4A described in Modification 1-1 instead of the intraductal imaging situation analyzing unit 4. In this case, the integral determining unit 52 performs integral determination depending on the magnitude of the inner wall gradient.

In the case where the average magnitude of the inner wall gradients is not less than the predetermined threshold, the image of the ductal inner wall is captured obliquely, and the abnormal region tends to appear as an image that is shorter in the direction of the inner wall gradient (depth direction) and longer in the direction orthogonal to the direction of the inner wall gradient as illustrated in FIG. 1. Therefore, the accuracy of abnormal region detection based on the feature value calculated from a region of a similar shape is expected to be high. In such a case, the integral determining unit 52 performs determination while attaching importance to the specific region discrimination index that is based on the feature value calculated from a region longer in the direction orthogonal to the direction of the inner wall gradient.

In the case where the average magnitude of the inner wall gradients is less than the predetermined threshold, the image of the ductal inner wall is captured from the front, where the aforementioned change in image length does not occur as depicted in FIG. 2. In such a case, the integral determining unit 52 performs determination while attaching importance to the specific region discrimination index that is based on the feature value calculated from a circular region not dependent on the direction.

While the hereinabove describes the shape in oblique imaging, in the oblique imaging situation the image also changes in the rotation direction depending on the vertical position of the part capturing the image. In this case, the integral determining unit 52 may perform determination while attaching importance to the specific region discrimination index that is based on the feature value calculated from a region in a direction according to the direction of the inner wall gradient.

In Modification 1-2, the intraductal imaging situation analyzing unit 4 may further include the inner wall gradient calculating unit 42 described in Modification 1-1. In this case, the integral determining unit 52 performs integral determination depending on the direction of the ductal deep region and the direction of the inner wall gradient.

Figure 12:
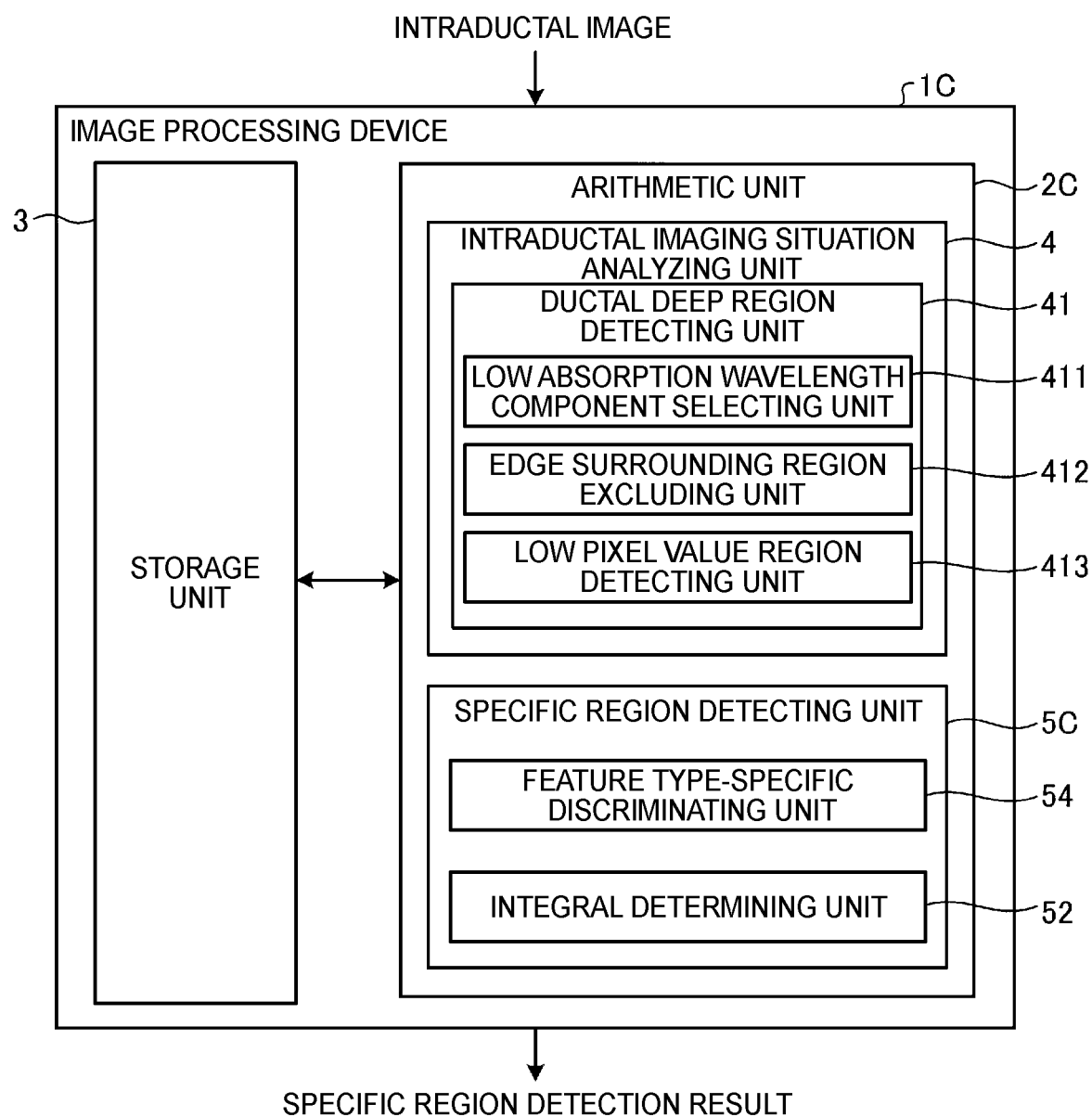
FIG. 12 is a block diagram illustrating the functional structure of an image processing device according to Modification 1-3 of the first Embodiment.

FIG. 12 is a block diagram illustrating the functional structure of an image processing device according to Modification 1-3 of the first Embodiment. In an image processing device 1C illustrated in FIG. 12, the structural elements having the same functions as those in the image processing device 1 illustrated in FIG. 3 are given the same reference signs as in FIG. 3.

The image processing device 1C includes an arithmetic unit 2C and the storage unit 3. The arithmetic unit 2C includes the intraductal imaging situation analyzing unit 4 and a specific region detecting unit 5C.

The specific region detecting unit 5C includes a feature type-specific discriminating unit 54 that calculates a plurality of specific region discrimination indices based on feature values different in type, and the integral determining unit 52. The feature type-specific discriminating unit 54 can set a feature value calculation region at any position in the image, and can calculate a plurality of specific region discrimination indices for feature values such as color, contour, pixel value surface shape, and texture.

The integral determining unit 52 performs integral determination while changing the specific region discrimination index to be attached importance depending on the presence or absence of the ductal deep region. In the case where the ductal deep region is in the image, the image of the ductal inner wall is captured obliquely, and so the contour of the specific region surface is clear as seen best in FIG. 1. Therefore, the accuracy of specific region detection based on the contour feature value is expected to be high. In such a case, the integral determining unit 52 performs determination while attaching importance to the specific region discrimination index that is based on the contour feature value.

In the case where the ductal deep region is not in the image, the image of the ductal inner wall is captured from the front, and so the contour of the specific region surface tends to be unclear as compared with the oblique imaging state (see for example, FIG. 2). Meanwhile, the pixel value surface shape (pixel value gradient) or texture can be easily captured. Therefore, the accuracy of specific region detection based on the pixel value surface shape feature value or the texture feature value is expected to be high. In such a case, the integral determining unit 52 can perform integral determination while attaching importance to the specific region discrimination index that is based on the pixel value surface shape feature value or the texture feature value.

Figure 13:
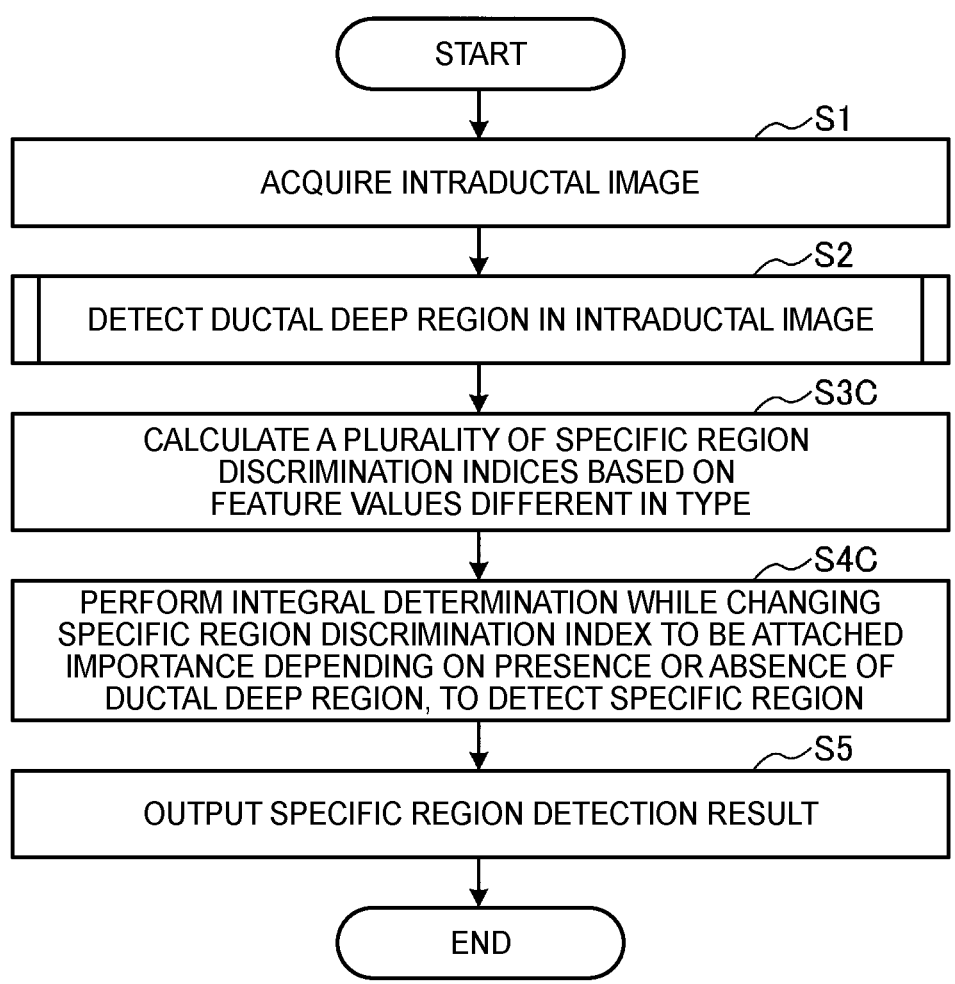
FIG. 13 is a flowchart illustrating the process performed by the image processing device according to Modification 1-3 of the first Embodiment.

FIG. 13 is a flowchart illustrating the process performed by the image processing device 1C. In FIG. 13, the same processes as those in the flowchart illustrated in FIG. 4 are given the same step numbers. The following describes the processes after step S2.

In step S3C, the feature type-specific discriminating unit 54 calculates the plurality of specific region discrimination indices based on the feature values different in type (step S3C).

Next in step S4C, the integral determining unit 52 performs integral determination while changing the specific region discrimination index to be attached importance depending on the presence or absence of the ductal deep region, to detect the specific region.

Finally, in step S5, the arithmetic unit 2C outputs the specific region detection result. The image processing device 1C thus completes the series of processes. The ductal deep region detection process in step S2 and the specific region discrimination index calculation process in step S3C may be performed in reverse order or concurrently.

According to Modification 1-3 described hereinabove, the plurality of specific region discrimination indices of the feature values different in type can be integrally determined depending on the presence or absence of the ductal deep region. Given that the image varies due to the difference in imaging direction (oblique, front, and the likes) to the ductal inner wall, the specific region can be detected accurately by attaching importance to the specific region discrimination index that is based on the more effective feature value.

In Modification 1-3, the image processing device 1C may include the intraductal imaging situation analyzing unit 4A described in Modification 1-1 instead of the intraductal imaging situation analyzing unit 4. In this case, the integral determining unit 52 performs integral determination while changing the specific region discrimination index to be attached importance depending on the magnitude of the inner wall gradient.

In the case where the average magnitude of the inner wall gradients is not less than the predetermined threshold, the image of the ductal inner wall is captured obliquely, and so the contour of the specific region surface is clear (see FIG. 1). In such a case, the integral determining unit 52 performs determination while attaching importance to the specific region discrimination index that is based on the contour feature value.

In the case where the average magnitude of the inner wall gradients is less than the predetermined threshold, the image of the ductal inner wall is captured from the front, and so the contour of the abnormal region surface tends to be unclear as compared with the oblique imaging state (see FIG. 2). Meanwhile, the pixel value surface shape (pixel value gradient) or texture can be easily captured. In such a case, the integral determining unit 52 performs integral determination while attaching importance to the specific region discrimination index that is based on the pixel value surface shape feature value or the texture feature value.

In Modification 1-3, the intraductal imaging situation analyzing unit 4 may further include the inner wall gradient calculating unit 42 described in Modification 1-1. In this case, the integral determining unit 52 performs integral determination depending on the presence or absence of the ductal deep region and the magnitude of the inner wall gradient.

Figure 14:
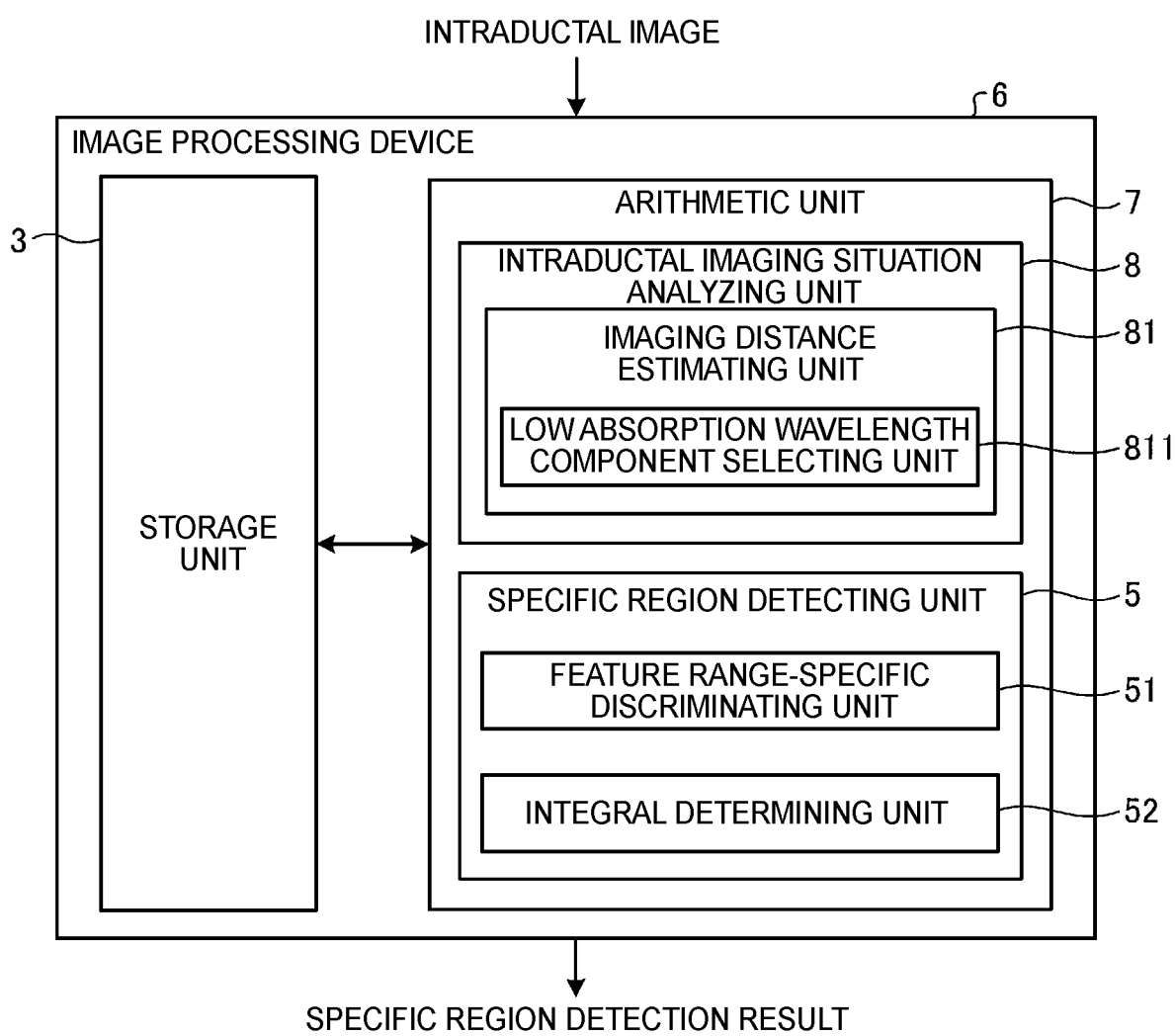
FIG. 14 is a block diagram illustrating the functional structure of an image processing device according to a second Embodiment.

FIG. 14 is a block diagram illustrating the operational structure of an image processing device according to the second Embodiment. In an image processing device 6 illustrated in FIG. 14, the structural elements having the same functions as those in the image processing device 1 illustrated in FIG. 3 are given the same reference signs as in FIG. 3.

The image processing device 6 includes an arithmetic unit 7 and the storage unit 3. The arithmetic unit 7 includes an intraductal imaging situation analyzing unit 8 and the specific region detecting unit 5.

The intraductal imaging situation analyzing unit 8 includes an imaging distance estimating unit 81 that estimates the imaging distance to the ductal inner wall. Various methods of imaging distance estimation are known. Embodiment 2 describes an imaging distance estimation method that assumes the imaging object as a uniform diffuser, or lambertian surface, as an example.

The imaging distance estimating unit 81 includes a low absorption wavelength component selecting unit 811 that selects a low absorption wavelength component with the lowest degree of absorption and scattering in the living body. This is intended to prevent a decrease in pixel value due to blood vessels and the like shown on the mucosal surface to obtain pixel value information that correlates most closely with the imaging distance to the mucosal surface. For example, in the case where the image is composed of R, G, and B components, the R component can be selected as described in the first Embodiment.

The imaging distance estimating unit 81 estimates the imaging distance assuming a uniform diffuser, based on the pixel value of the selected low absorption wavelength component. Specifically, the imaging distance estimating unit 81 estimates imaging distance r in a plurality of locations in the intraductal image according to the following Formula (2).

$$r = \sqrt{\frac{I \times K \times \cos\theta}{L}} \quad (2)$$

In the right side of Formula (2), letter I is the radiation intensity of the light source measured beforehand, K is the diffuse reflection coefficient of the mucosal surface, θ is the angle between a normal vector to the mucosal surface and a vector from the surface to the light source, and L is the R component value of the pixel showing the mucosal surface subjected to the imaging distance estimation. Diffuse reflection coefficient K is obtained by measuring the average value beforehand. Angle θ is an average value set beforehand as the value determined from the positional relationship between the tip of the endoscope and the mucosal surface.

Instead of estimating imaging distance r defined by Formula (2), the imaging distance estimating unit 81 may perform an adaptive process in a subsequent stage using the pixel value that correlates with imaging distance r.

In the case where the average value of the imaging distances calculated in the plurality of locations by the imaging distance estimating unit 81 is less than a predetermined threshold, the imaging distance is relatively short. In the case where the imaging distance is short, the subject appears larger than in the case where the imaging distance is long. In such a case, the integral determining unit 52 performs integral determination while attaching importance to the specific region discrimination index that is based on the feature value of a large feature value calculation range.

In the case where the average value of the imaging distances is not less than the predetermined threshold, the imaging distance is relatively long, and the subject appears relatively small. in addition, in the case where the range of the region used for feature value calculation is large, there is a possibility of a decrease in detection accuracy caused by the inclusion of such a region (specular reflection, residue, bubble, normal fold, etc.) that leads to lower accuracy. In such a case, the integral determining unit 52 can perform determination while attaching importance to the specific region discrimination index that is based on the feature value of a small feature value calculation range.

Figure 15:
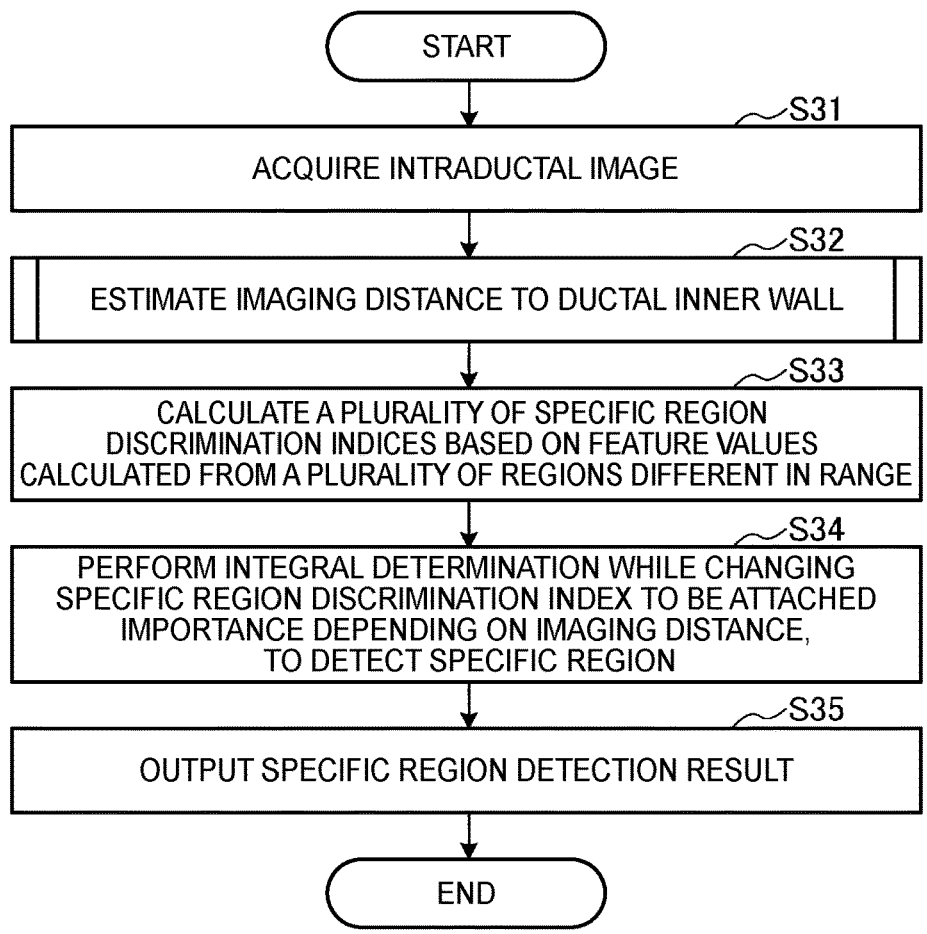
FIG. 15 is a flowchart illustrating the process performed by the image processing device according to the second Embodiment.

FIG. 15 is a flowchart roughly illustrating the process performed by the image processing device 6. First in step S31, the arithmetic unit 7 acquires the intraductal image to be processed. Next in step S32, the imaging distance estimating unit 81 estimates the imaging distance to the ductal inner wall.

Figure 16:
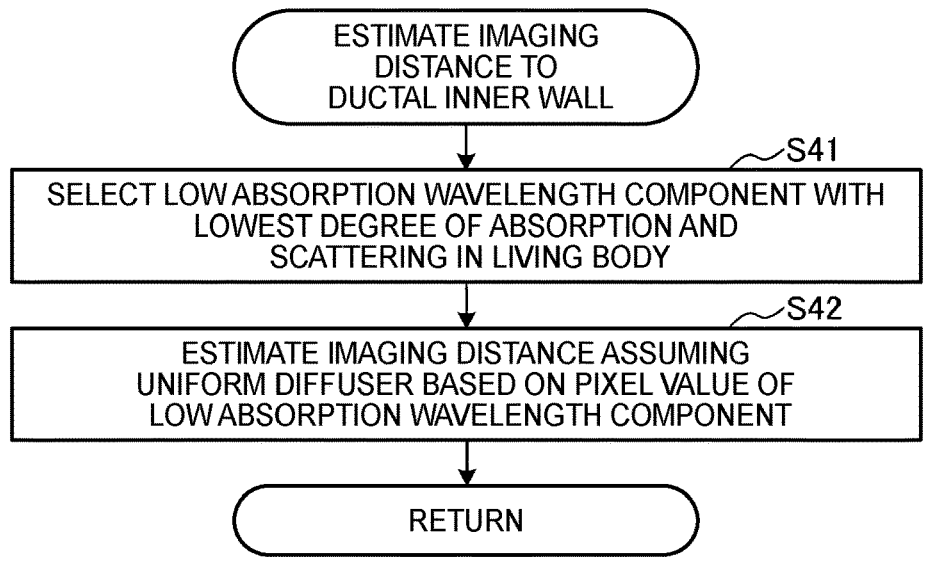
FIG. 16 is a flowchart illustrating the process performed by an imaging distance estimating unit in the image processing device according to the second Embodiment.

FIG. 16 is a flowchart illustrating the process performed by the imaging distance estimating unit 81. The process by the imaging distance estimating unit 81 is described below, with reference to FIG. 16. First in step S41, the low absorption wavelength component selecting unit 811 selects the low absorption wavelength component with the lowest degree of absorption and scattering in the living body.

Next in step S42, the imaging distance estimating unit 81 estimates the imaging distance assuming a uniform diffuser based on the pixel value of the selected low absorption wavelength component. Specifically, the imaging distance estimating unit 81 estimates the imaging distance according to the foregoing Formula (2). This completes the imaging distance estimation process by the imaging distance estimating unit 81 in step S32.

The arithmetic unit 7 may perform processes such as correcting pixel value inconsistency caused by an optical system or an illumination system or excluding non-mucosal regions which include specular reflection, residue, and bubble, before the imaging distance estimation process by the imaging distance estimating unit 81. Lower accuracy of the subsequent processes can be prevented in this way.

Moreover, the endoscope may be provided with detection means such as a distance measurement sensor, where the imaging distance estimating unit 81 estimates the imaging distance based on the detection result.

After step S32, the feature range-specific discriminating unit 51 calculates the plurality of specific region discrimination indices based on the feature values calculated from the plurality of regions different in range as noted in step S33. This process is the same as the process of step S3 described in the first Embodiment.

Next in step S34, the integral determining unit 52 performs integral determination while changing the specific region discrimination index to be attached importance depending on the imaging distance, to detect the specific region.

Finally, in step S35, the arithmetic unit 7 outputs the specific region detection result. The image processing device 6 thus completes the series of processes. The imaging distance estimation process in step S32 and the specific region discrimination index calculation process in step S33 may be performed in reverse order or concurrently.

According to the second Embodiment described hereinabove, the plurality of specific region discrimination indices of different feature value calculation ranges can be integrally determined depending on the imaging distance. Given that the image varies due to the difference in imaging distance to the ductal inner wall, the specific region can be detected accurately by attaching importance to the specific region discrimination index that is based on the more effective feature value.

Figure 17:
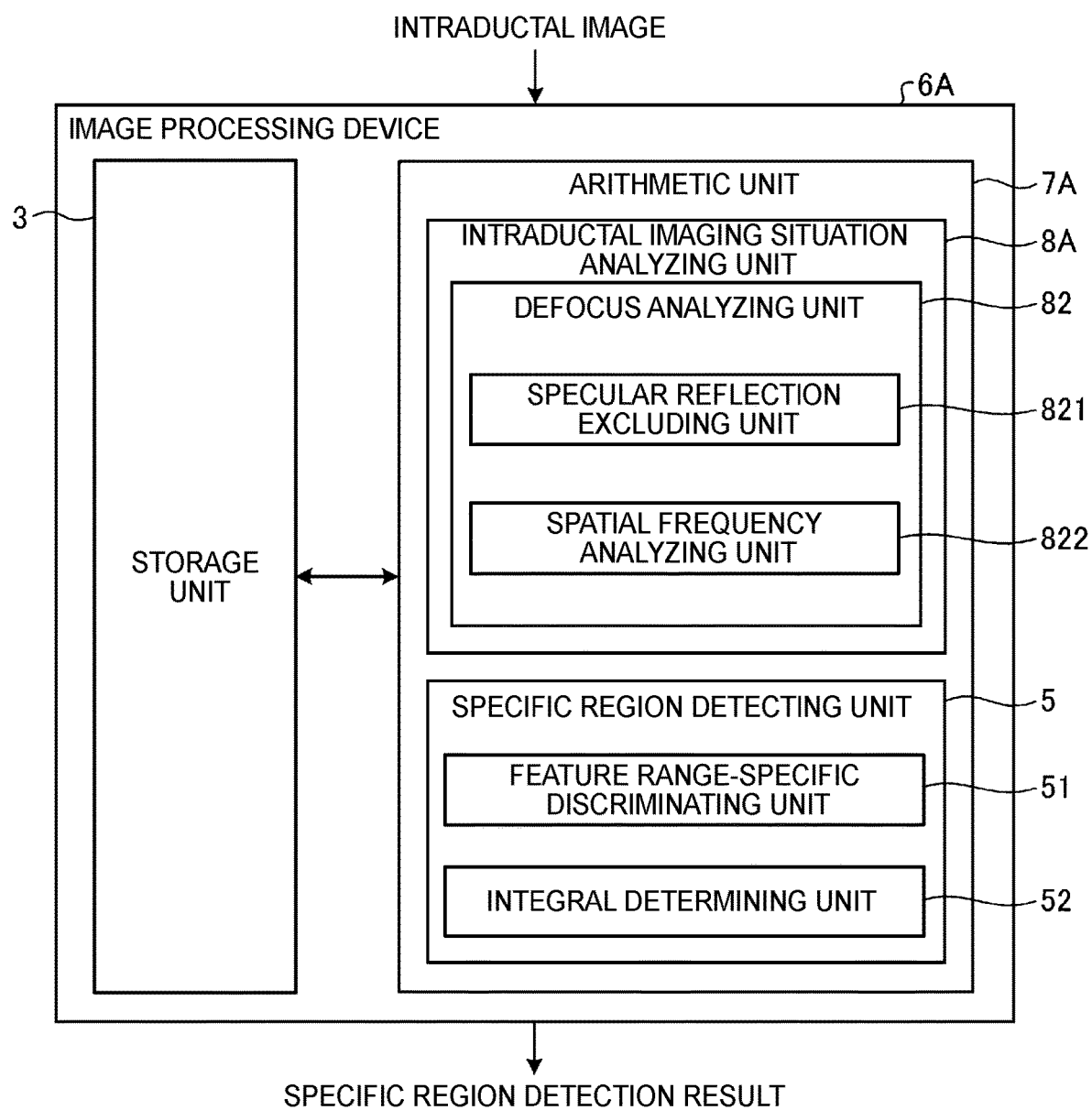
FIG. 17 is a block diagram illustrating the functional structure of an image processing device according to Modification 2-1 of the second Embodiment.

FIG. 17 is a block diagram illustrating the functional structure of an image processing device according to Modification 2-1 of the second Embodiment. In an image processing device 6A illustrated in FIG. 17, the structural elements having the same functions as those in the image processing device 6 illustrated in FIG. 14 are given the same reference signs as in FIG. 14.

The image processing device 6A includes an arithmetic unit 7A and the storage unit 3. The arithmetic unit 7A includes an intraductal imaging situation analyzing unit 8A and the specific region detecting unit 5.

The intraductal imaging situation analyzing unit 8A includes a defocus analyzing unit 82 that analyzes defocus in the intraductal image. The defocus analyzing unit 82 includes a specular reflection excluding unit 821 and a spatial frequency analyzing unit 822.

The specular reflection excluding unit 821 distinguishes and excludes specular reflection in the intraductal image, for example based on a method disclosed in Japanese Patent Application No. 2012-11137.

The spatial frequency analyzing unit 822 performs known two-dimensional Fourier transform (the general theory is described in Reference: Two-dimensional Fourier Transform, "Digital Image Processing," p. 128, CG-ARTS Society) on a predetermined component (e.g. G component) in the intraductal image to obtain a Fourier spectrum, and then calculates a spectrum sum in annular regions whose distance from the center indicating a low frequency component is in a predetermined range while changing the distance, thus obtaining a radial distribution. In the radial distribution, a part with a short distance represents a low frequency component in the intraductal image, and a part with a long distance represents a high frequency component in the intraductal image. Typically, an image with few high frequency components is significantly defocused.

Figure 18:
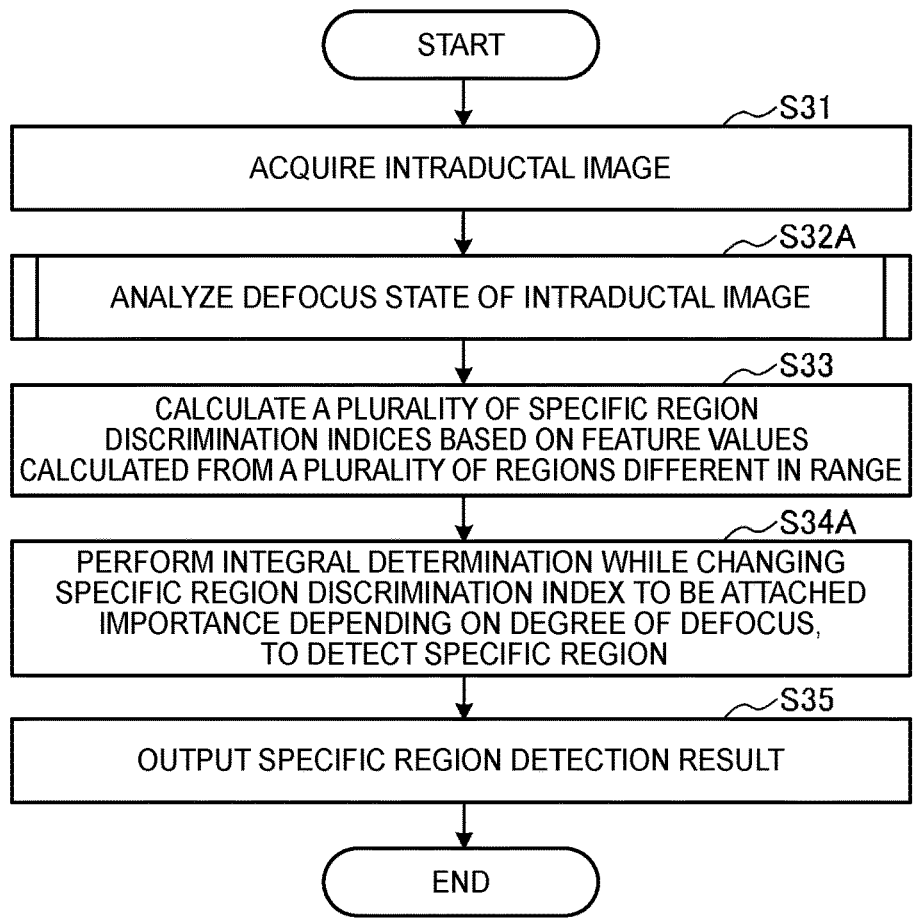
FIG. 18 is a flowchart illustrating the process performed by the image processing device according to Modification 2-1 of the second Embodiment.

FIG. 18 is a flowchart illustrating the process performed by the image processing device 6A. In FIG. 18, the same processes as those in the flowchart illustrated in FIG. 15 are given the same step numbers. The following describes the processes after step S31.

Figure 19:
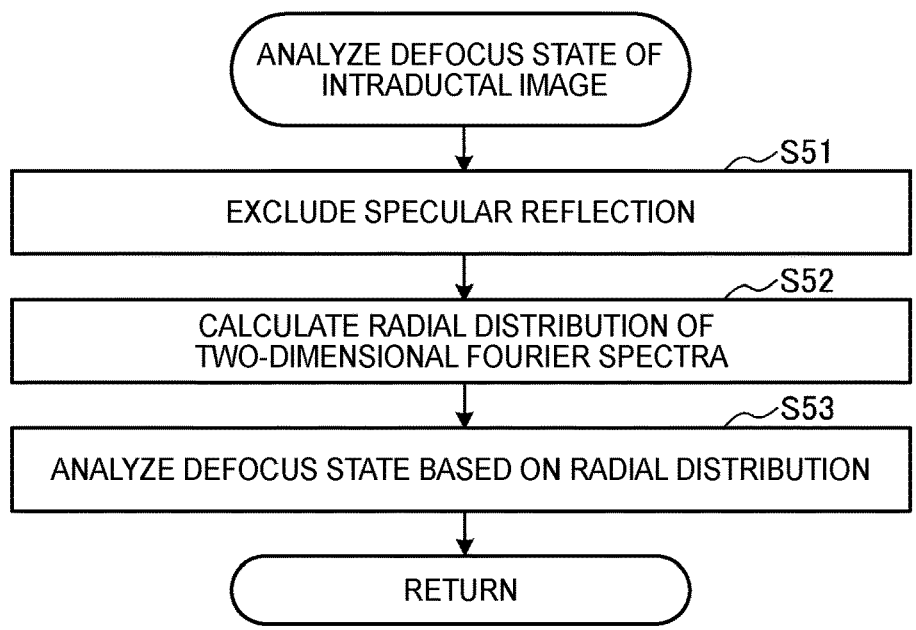
FIG. 19 is a flowchart illustrating the process performed by a defocus analyzing unit in the image processing device according to Modification 2-1 of the second Embodiment.

In step S32A, the defocus analyzing unit 82 analyzes the defocus state of the intraductal image (step S32A). FIG. 19 is a flowchart illustrating the process performed by the defocus analyzing unit 82. The process by the defocus analyzing unit 82 is described below, with reference to FIG. 19. First in step S51, the specular reflection excluding unit 821 distinguishes and excludes specular reflection in the intraductal image.

Next in step S52, the spatial frequency analyzing unit 822 performs two-dimensional Fourier transform on the predetermined component of the intraductal image, and then calculates the radial distribution of the two-dimensional Fourier spectrum obtained by the two-dimensional Fourier transform.

Finally, in step S53, the defocus analyzing unit 82 analyzes the defocus state based on the radial distribution of the two-dimensional Fourier spectrum. Specifically, the defocus analyzing unit 82 determines that the degree of defocus is larger when the intraductal image has fewer high frequency components (i.e., part with a long distance in the radial distribution).

After step S32A, the feature range-specific discriminating unit 51 calculates the plurality of specific region discrimination indices based on the feature values calculated from the plurality of regions different in range as noted in step S33.

Next in step S34A, the integral determining unit 52 performs integral determination while changing the specific region discrimination index to be attached importance depending on the degree of defocus, to detect the specific region. In the case where the degree of defocus is larger, the subject image has a wider range than in the case where the degree of defocus is smaller. The integral determining unit 52 performs integral determination while attaching importance to the specific region discrimination index that is based on the feature value of a larger feature value calculation range, when the degree of defocus is larger.

Finally, in step S35, the arithmetic unit 7A outputs the specific region detection result. The image processing device 6A thus completes the series of processes. The defocus state analysis process in step S32A and the specific region discrimination index calculation process in step S33 may be performed in reverse order or concurrently.

According to Modification 2-1 described above, the plurality of specific region discrimination indices of different feature value calculation ranges can be integrally determined depending on the degree of defocus. Given that the image varies due to defocus, the specific region can be detected accurately by attaching importance to the specific region discrimination index that is based on the more effective feature value.

In Modification 2-1, the intraductal imaging situation analyzing unit 8A may further include the imaging distance estimating unit 81 described in the second Embodiment. In this case, the integral determining unit 52 can perform integral determination depending on the imaging distance and the degree of defocus.

Figure 20:
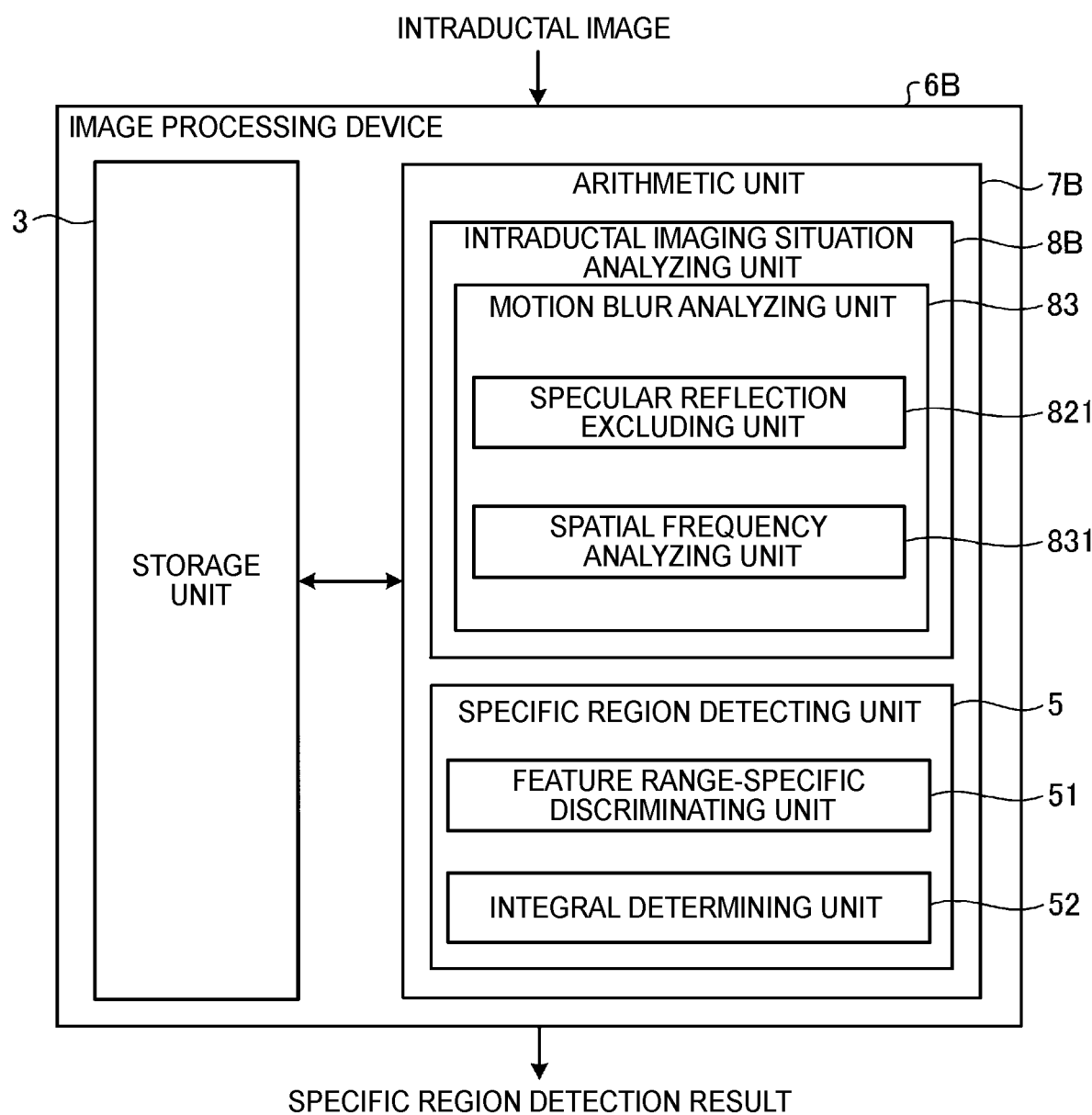
FIG. 20 is a block diagram illustrating the functional structure of an image processing device according to Modification 2-2 of the second Embodiment.

FIG. 20 is a block diagram illustrating the functional structure of an image processing device according to Modification 2-2 of the second Embodiment. In an image processing device 6B illustrated in FIG. 20, the structural elements having the same functions as those in the image processing device 6A illustrated in FIG. 17 are given the same reference signs as in FIG. 17.

The image processing device 6B includes an arithmetic unit 7B and the storage unit 3. The arithmetic unit 7B includes an intraductal imaging situation analyzing unit 8B and the specific region detecting unit 5.

The intraductal imaging situation analyzing unit 8B includes a motion blur analyzing unit 83 that analyzes motion blur in the intraductal image. The motion blur analyzing unit 83 includes the specular reflection excluding unit 821 and a spatial frequency analyzing unit 831.

The spatial frequency analyzing unit 831 calculates the angular distribution and radial distribution of a two-dimensional Fourier spectrum. Specifically, the spatial frequency analyzing unit 831 performs two-dimensional Fourier transform on a predetermined component (e.g. G component) in the intraductal image to obtain a two-dimensional Fourier spectrum, and then calculates a spectrum sum in fan-shaped regions whose angle to the horizontal line passing through the center indicating a low frequency component is in a predetermined range while changing the angle, thus obtaining an angular distribution. The spatial frequency analyzing unit 831 can also use the same method as described in Modification 2-1 in the fan-shaped regions whose angle is in the predetermined range, thus obtaining a radial distribution in the fan-shaped regions whose angle is in the predetermined range.

Figure 21:
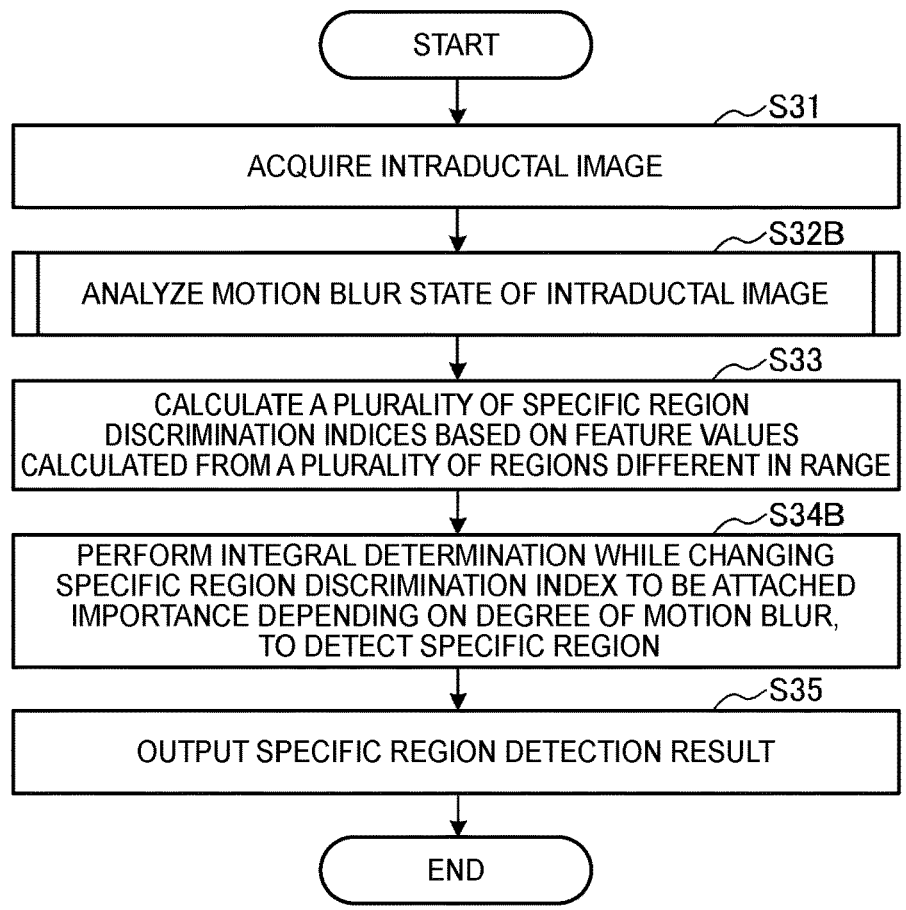
FIG. 21 is a flowchart illustrating the process performed by the image processing device according to Modification 2-2 of the second Embodiment.

FIG. 21 is a flowchart illustrating the process performed by the image processing device 6B. In FIG. 21, the same processes as those in the flowchart illustrated in FIG. 15 are given the same step numbers. The following describes the processes after step S31.

Figure 22:
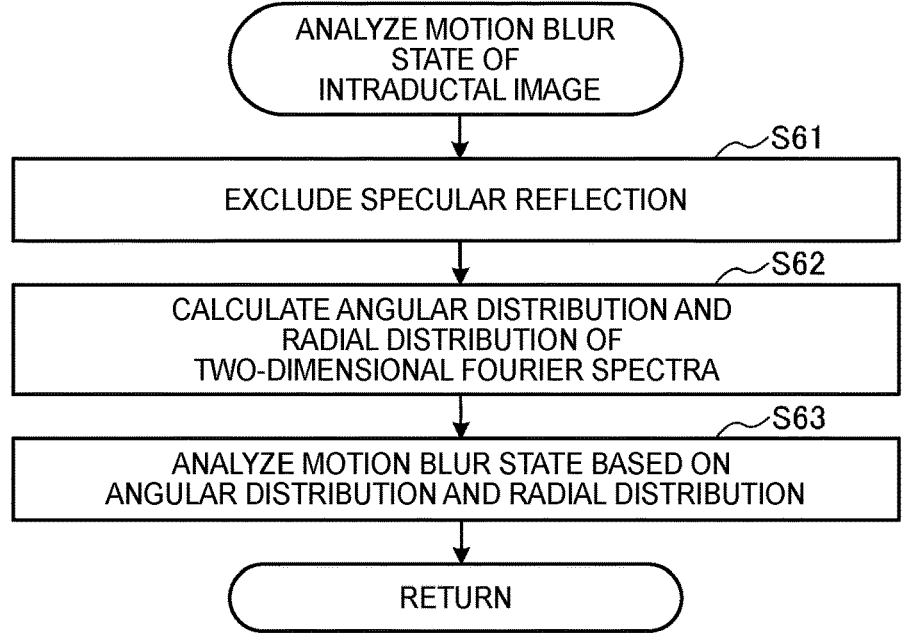
FIG. 22 is a flowchart illustrating the process performed by a motion blur analyzing unit in the image processing device according to Modification 2-2 of the second Embodiment.

In step S32B, the motion blur analyzing unit 83 analyzes the motion blur state of the intraductal image. FIG. 22 is a flowchart roughly illustrating the process performed by the motion blur analyzing unit 83. The process by the motion blur analyzing unit 83 is described below, with reference to FIG. 22. First in step S61, the specular reflection excluding unit 821 excludes specular reflection in the intraductal image.

Next in step S62, the spatial frequency analyzing unit 831 calculates the angular distribution and radial distribution of the two-dimensional Fourier spectrum.

In step S63, the motion blur analyzing unit 83 analyzes the motion blur state based on the angular distribution and the radial distribution. Specifically, the motion blur analyzing unit 83 analyzes the motion blur direction based on the angular distribution, and analyzes the motion blur state based on the radial distribution of a region whose angle is narrowed down according to the motion blur direction analysis result. For example, in the case where motion blur occurs substantially in one direction, the spectrum distribution is relatively high in the angular direction corresponding to that direction. In this case, the motion blur analyzing unit 83 analyzes the motion blur state based on the radial distribution near the region where the spectrum distribution is relatively high.

Endoscopes have an imaging method called a frame sequential method. In this imaging method, one image sensor captures an image while sequentially applying illumination light of R, G, and B in chronological order. In such a case, motion blur may be limited to one wavelength component, or occur between wavelength components. Hence, in the case of the frame sequential method, the motion blur analyzing unit 83 can analyze motion blur in each wavelength component of R, G, and B, and can also analyze motion blur between wavelength components. The analysis of motion blur between wavelength components may be carried out by taking a sum of images of wavelength components to generate a synthetic image and applying the aforementioned spatial frequency analysis or the like to the synthetic image.

After step S32B, the feature range-specific discriminating unit 51 calculates the plurality of specific region discrimination indices based on the feature values calculated from the plurality of regions different in range as noted in step S33.

Next in step S34B, the integral determining unit 52 performs integral determination while changing the specific region discrimination index to be attached importance depending on the degree of motion blur, to detect the specific region. In the case where the degree of motion blur is larger, the subject image has a wider range than in the case where the degree of motion blur is smaller. The integral determining unit 52 performs integral determination while attaching importance to the specific region discrimination index that is based on the feature value of a larger feature value calculation range, when the degree of motion blur is larger.

Finally, in step S35, the arithmetic unit 7B outputs the specific region detection result. The image processing device 6B thus completes the series of processes. The motion blur state analysis process in step S32B and the specific region discrimination index calculation process in step S33 may be performed in reverse order or concurrently.

According to Modification 2-2 described above, the plurality of specific region discrimination indices of different feature value calculation ranges can be integrally determined depending on the motion blur state (I.e., direction and degree). Given that the image varies due to motion blur, the specific region can be detected accurately by attaching importance to the specific region discrimination index that is based on the more effective feature value.

In Modification 2-2, the process of excluding specular reflection may be omitted.

In Modification 2-2, the intraductal imaging situation analyzing unit 8B may further include the imaging distance estimating unit 81 described in Embodiment 2 and/or the defocus analyzing unit 82 described in Modification 2-1. In this case, the integral determining unit 52 performs integral determination depending on the imaging distance and/or the degree of defocus and the degree of motion blur.

Figure 23:
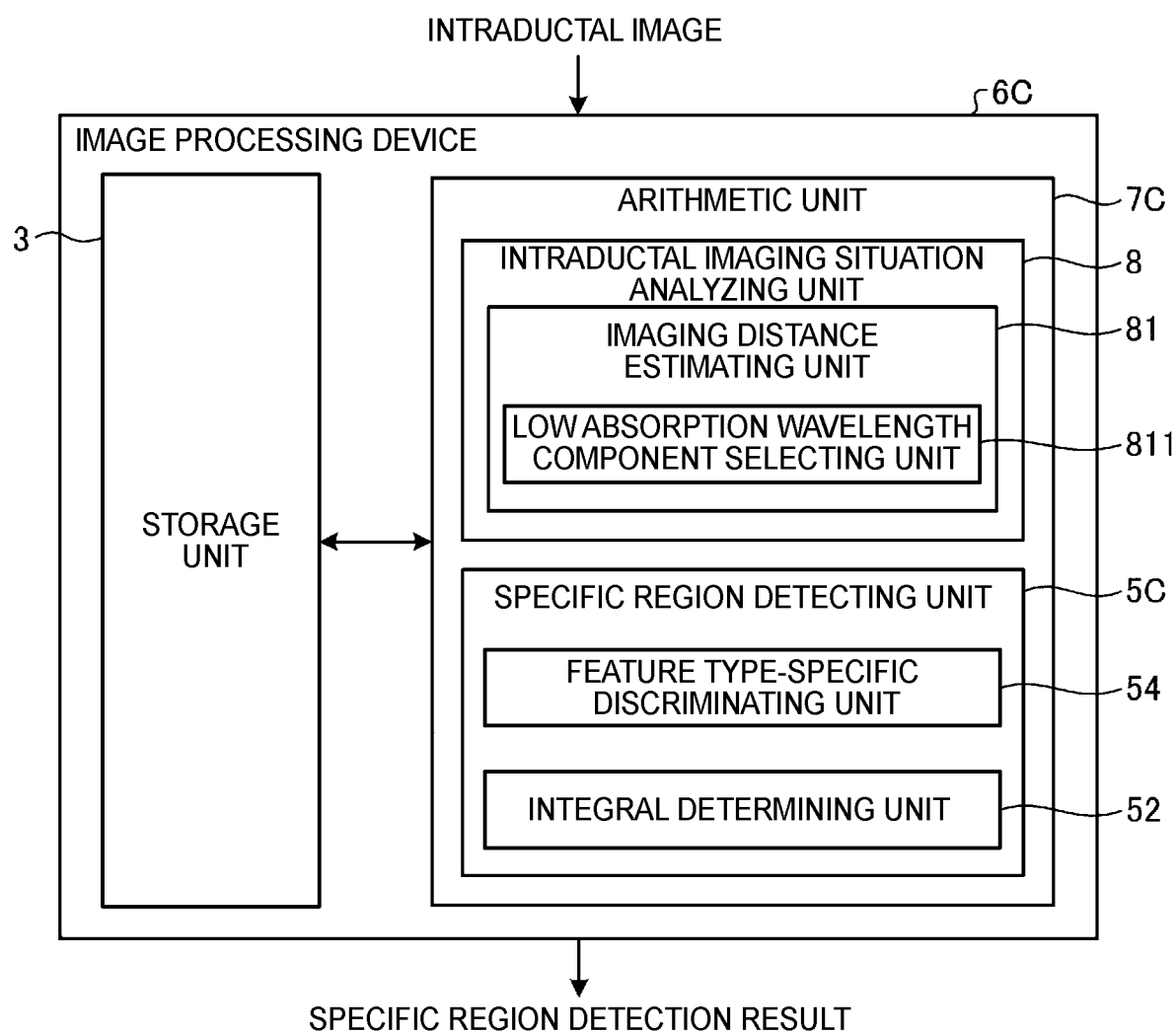
FIG. 23 is a block diagram illustrating the functional structure of an image processing device according to Modification 2-3 of the second Embodiment.

FIG. 23 is a block diagram illustrating the functional structure of an image processing device according to Modification 2-3 of the second Embodiment. In an image processing device 6C illustrated in FIG. 23, the structural elements having the same functions as those in the image processing device 1C illustrated in FIG. 12 and the image processing device 6 illustrated in FIG. 14 are given the same reference signs as in FIGS. 12 and 14.

The image processing device 6C includes an arithmetic unit 7C and the storage unit 3. The arithmetic unit 7C includes the intraductal imaging situation analyzing unit 8 and the specific region detecting unit 5C.

The specific region detecting unit 5C includes the feature type-specific discriminating unit 54 and the integral determining unit 52.

The integral determining unit 52 performs integral determination while changing the specific region discrimination index to be attached or assigned importance depending on the imaging distance, to detect the specific region. In the case where the average value of the imaging distances calculated in the plurality of locations is less than a predetermined threshold, i.e. in the case where the imaging distance is short, the texture and contour of the specific region surface appear clear. In such a case, the integral determining unit 52 performs integral determination while attaching importance to the specific region discrimination index that is based on the texture feature value or the contour feature value.

In the case where the average value of the imaging distances is not less than the predetermined threshold, i.e. in the case where the imaging distance is long, the texture tends to be unclear due to lower resolution, and the contour tends to be unclear due to dark part noise or the like. Meanwhile, the color and the pixel value surface shape can be kept relatively stable. Hence, the integral determining unit 52 can perform determination while attaching importance to the specific region discrimination index that is based on the color feature value or the pixel value surface shape feature value.

If the imaging distance is short, there is a possibility that any of the color components saturates (e.g., R component tends to saturate in a living body) and the color balance is lost. In view of this, the integral determining unit 52 may perform determination without attaching importance to the specific region discrimination index that is based on the color feature value.

Figure 24:
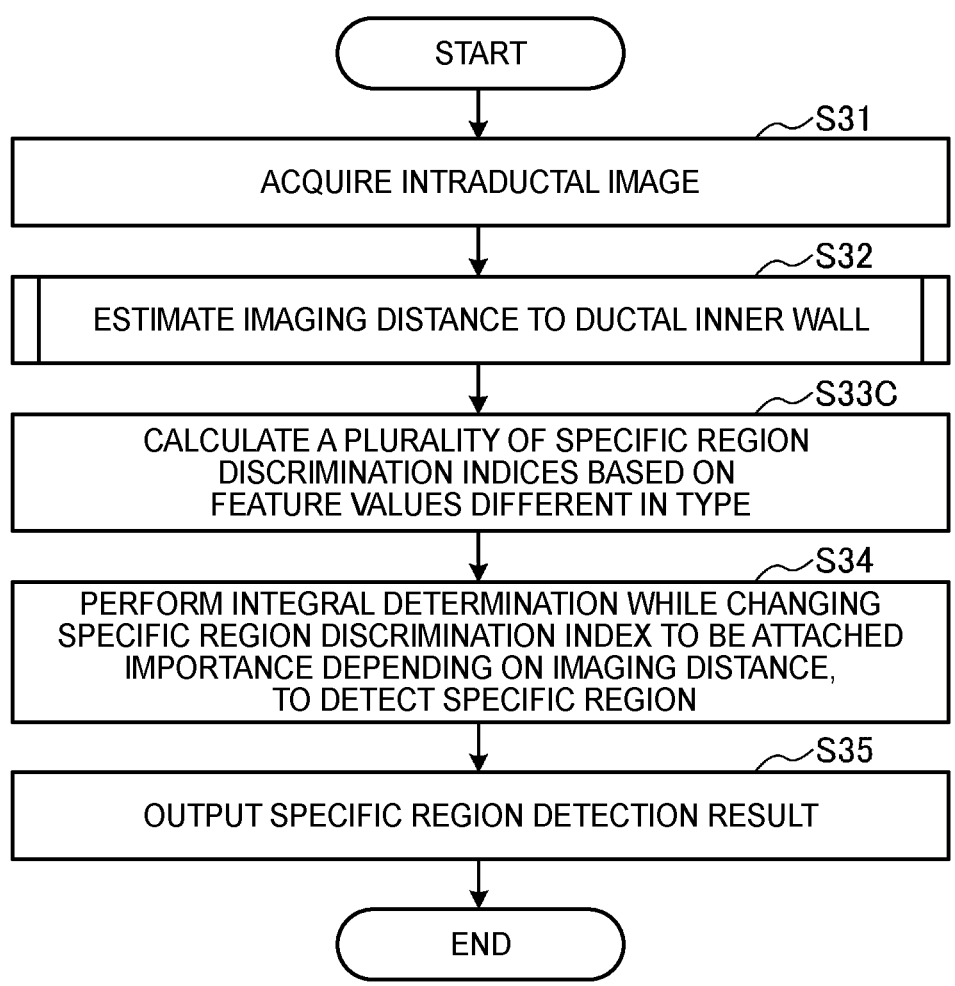
FIG. 24 is a flowchart illustrating the process performed by the image processing device according to Modification 2-3 of the second Embodiment.

FIG. 24 is a flowchart illustrating the process performed by the image processing device 6C. In FIG. 24, the same processes as those in the flowchart illustrated in FIG. 15 are given the same step numbers. The following describes the processes after step S32.

In step S33C, the feature type-specific discriminating unit 54 calculates the plurality of specific region discrimination indices based on the feature values different in type.

Next, the integral determining unit 52 performs integral determination while changing the specific region discrimination index to be attached or assigned importance depending on the imaging distance, to detect the specific region (step S34).

Finally, in step S35, the arithmetic unit 7C outputs the specific region detection result. The image processing device 6C thus completes the series of processes. The imaging distance estimation process in step S32 and the specific region discrimination index calculation process in step S33C may be performed in reverse order or concurrently.

According to Modification 2-3 described above, the plurality of specific region discrimination indices of the feature values different in type can be integrally determined depending on the imaging distance. Given that the image varies due to the difference in imaging distance, the specific region can be detected accurately by attaching importance to the specific region discrimination index that is based on the more effective feature value.

In Modification 2-3, the intraductal imaging situation analyzing unit 8 may be replaced with the intraductal imaging situation analyzing unit 8A including the defocus analyzing unit 82 or the intraductal imaging situation analyzing unit 8B including the motion blur analyzing unit 83.

In the case where the intraductal imaging situation analyzing unit 8A is included, the integral determining unit 52 performs integral determination while changing the specific region discrimination index to be attached importance depending on the degree of defocus. In the case where the degree of defocus is small, the texture and contour of the specific region surface appear clear. In such a case, the integral determining unit 52 performs integral determination while attaching importance to the specific region discrimination index that is based on the texture feature value or the contour feature value.

In the case where the degree of defocus is large, the texture and the contour tend to be unclear, but the color and the pixel value surface shape can be kept relatively stable. Hence, the integral determining unit 52 can perform determination while attaching importance to the specific region discrimination index that is based on the color feature value or the pixel value surface shape feature value.

In the case where the intraductal imaging situation analyzing unit 8B is included, the integral determining unit 52 performs integral determination while changing the specific region discrimination index to be attached importance depending on the degree of motion blur. In the case where the degree of motion blur is small, the texture and contour of the specific region surface appear clear. In such a case, the integral determining unit 52 performs integral determination while attaching importance to the specific region discrimination index that is based on the texture feature value or the contour feature value.

In the case where the degree of motion blur is large, the texture and the contour tend to be unclear, but the color and the pixel value surface shape can be kept relatively stable. Hence, the integral determining unit 52 can perform determination while attaching importance to the specific region discrimination index that is based on the color feature value or the pixel value surface shape feature value.

If motion blur occurs with the endoscope in the frame sequential method, color deviation takes place and the color feature value becomes unstable. In this case, the integral determining unit 52 may perform determination without attaching importance to the specific region discrimination index that is based on the color feature value.

In Modification 2-3, the intraductal imaging situation analyzing unit 8 may include any two or all of the imaging distance estimating unit 81, the defocus analyzing unit 82, and the motion blur analyzing unit 83.

Figure 25:
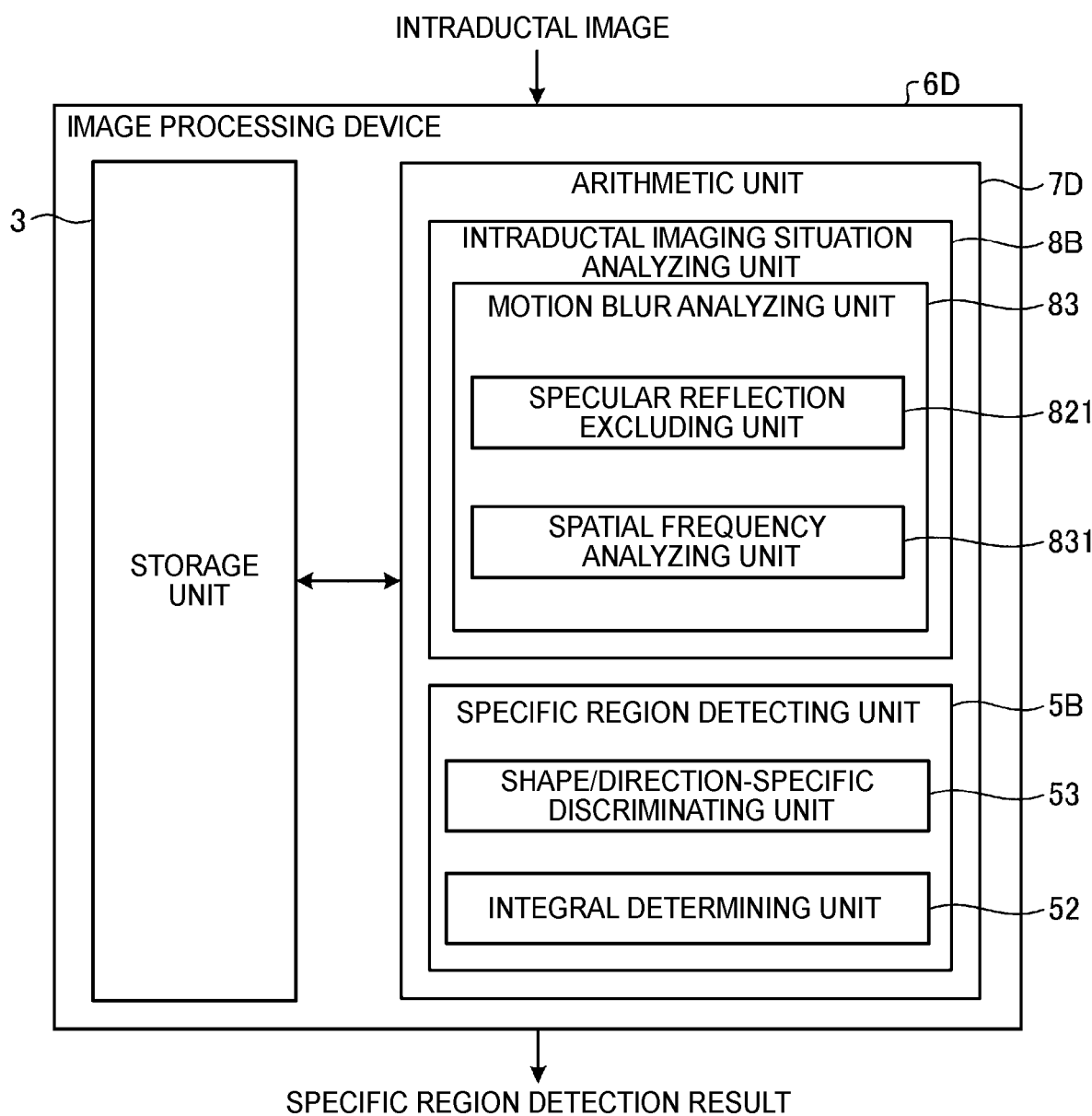
FIG. 25 is a block diagram illustrating the functional structure of an image processing device according to Modification 2-4 of the second Embodiment.

FIG. 25 is a block diagram illustrating the functional structure of an image processing device according to Modification 2-4 of the second Embodiment. In an image processing device 6D illustrated in FIG. 25, the structural elements having the same functions as those in the image processing device 1B illustrated in FIG. 9 and the image processing device 6B illustrated in FIG. 20 are given the same reference signs as in FIGS. 9 and 20.

The image processing device 6D includes an arithmetic unit 7D and the storage unit 3. The arithmetic unit 7D includes the intraductal imaging situation analyzing unit 8B and the specific region detecting unit 5B.

Figure 26:
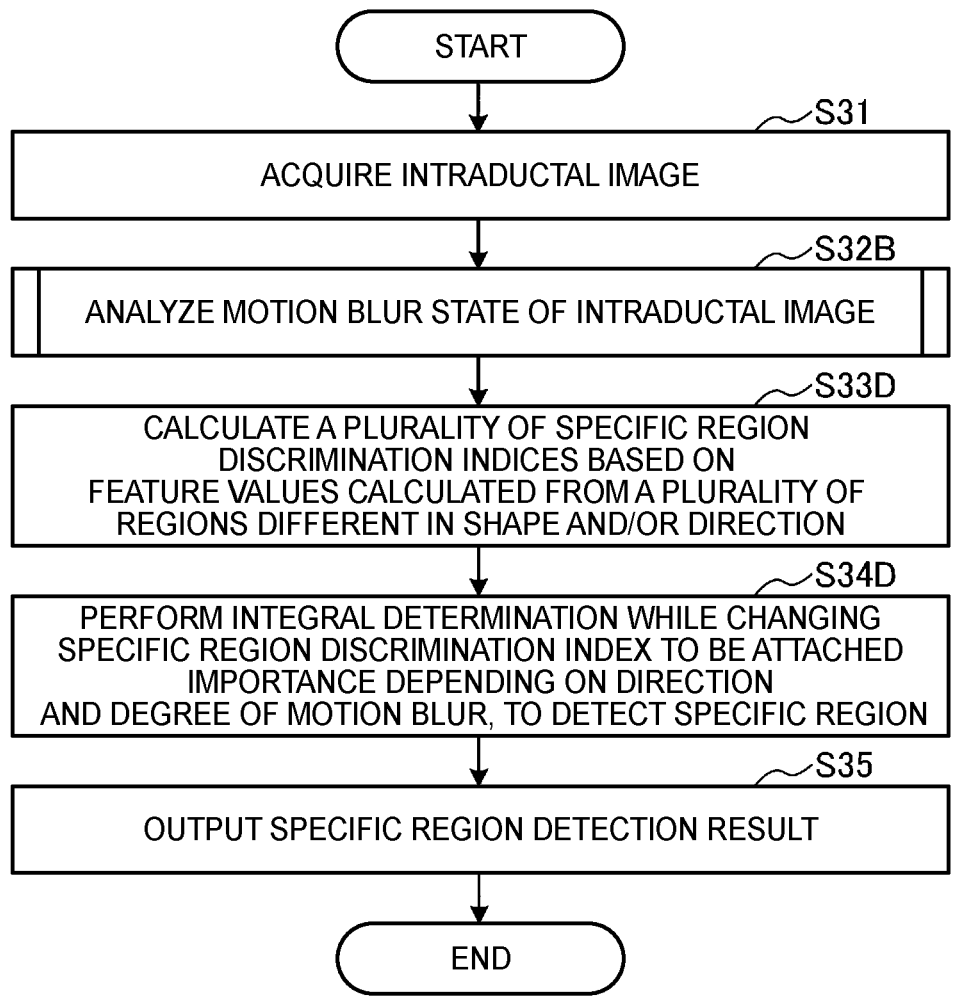
FIG. 26 is a flowchart illustrating the process performed by the image processing device according to Modification 2-4 of the second Embodiment.

FIG. 26 is a flowchart illustrating the process performed by the image processing device 6D. In FIG. 26, the same processes as those in the flowchart illustrated in FIG. 21 are given the same step numbers. The following describes the processes after step S32B.

In step S33D, the shape/direction-specific discriminating unit 53 calculates the plurality of specific region discrimination indices based on the feature values calculated from the plurality of regions different in shape and/or direction. For example, the shape/direction-specific discriminating unit 53 calculates the feature values from the plurality of regions using the feature value calculation region group 202 illustrated in FIG. 10.

Next in step S34D, the integral determining unit 52 performs integral determination while changing the specific region discrimination index to be attached importance depending on the direction and degree of motion blur, to detect the specific region. In the case where motion blur occurs, the imaging object appears to be extended by the degree (e.g., magnitude) of motion blur in the direction of motion blur. In such a case, the integral determining unit 52 performs integral determination while attaching importance to the specific region discrimination index that is based on the feature value calculated from a feature value calculation region whose shape is extended by the degree of motion blur in the direction of motion blur.

Finally, in step S35, the arithmetic unit 7D outputs the specific region detection result (step S35). The image processing device 6D thus completes the series of processes. The motion blur state analysis process in step S32B and the specific region discrimination index calculation process in step S33D may be performed in reverse order or concurrently.

According to Modification 2-4 described above, the plurality of specific region discrimination indices of the feature value calculation regions different in shape and/or direction can be integrally determined depending on the motion blur state. Given that the image varies due to motion blur, the specific region can be detected accurately by attaching importance to the specific region discrimination index that is based on the more effective feature value.

Figure 27:
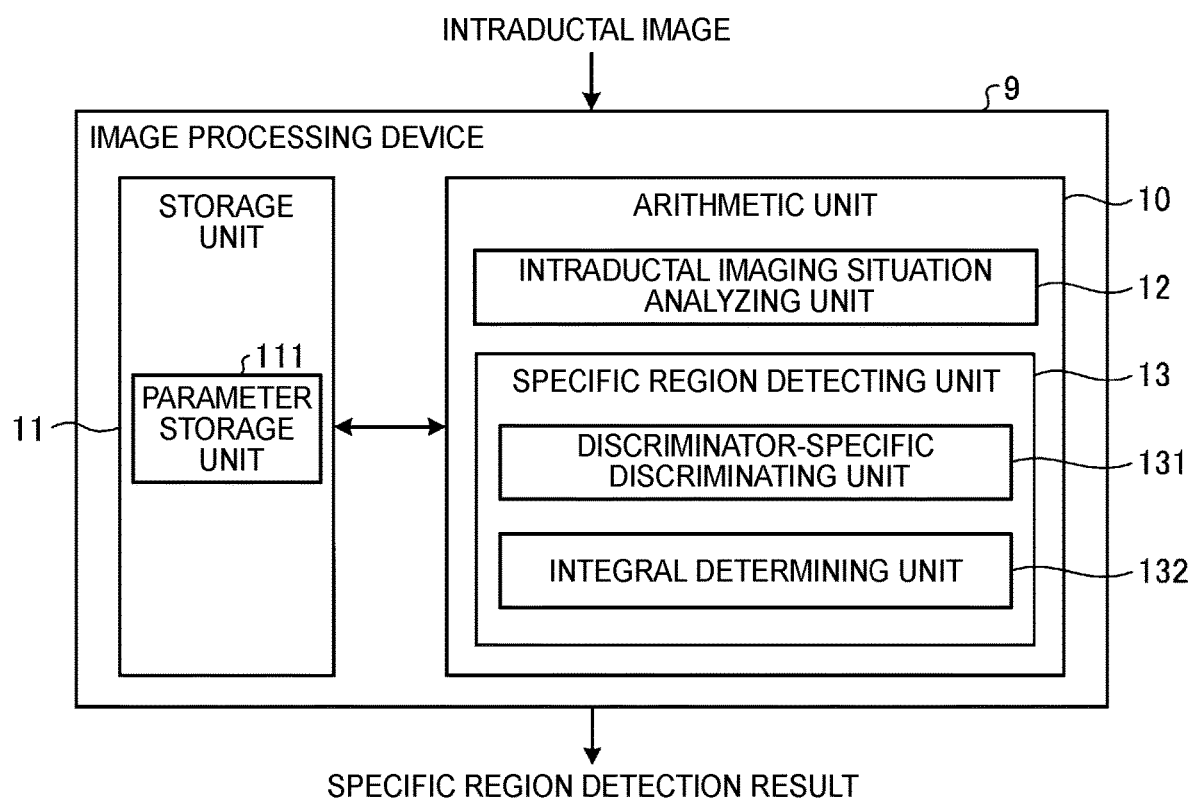
FIG. 27 is a block diagram illustrating the functional structure of an image processing device according to a third Embodiment.

FIG. 27 is a block diagram illustrating the functional structure of an image processing device according to the third Embodiment. An image processing device 9 illustrated in FIG. 27 includes an arithmetic unit 10, or calculation unit 10, and a storage unit 11. The arithmetic unit 10 includes an intraductal imaging situation analyzing unit 12 and a specific region detecting unit 13. The storage unit 11 includes a parameter storage unit 111.

The intraductal imaging situation analyzing unit 12 may be any one of the intraductal imaging situation analyzing units described in the respective first and second Embodiments, or any combination thereof.

The specific region detecting unit 13 includes a discriminator-specific discriminating unit 131 that calculates a plurality of specific region discrimination indices based on different discriminators and an integral determining unit 132 that performs integral determination while attaching importance to a specific region discrimination index that is based on a discriminator of a discrimination parameter generated using training data in an intraductal imaging situation identical to the analyzed intraductal imaging situation, to detect the specific region.

The discriminator-specific discriminating unit 131 first set a feature value calculation region at any position in the image. The discriminator-specific discriminating unit 131 then calculates a feature value from each feature value calculation region and, from these feature values, calculates a plurality of specific region discrimination indices that are based on discriminators different in discrimination parameter. A discrimination parameter mentioned here is, for example, a discriminating boundary in the feature space, a distribution model depending on the intraductal imaging situation, a discriminant function, or a representative pattern (e.g., a template). The term "identical" used here means to be substantially the same as the analysis result (the presence or absence of the deep region, the direction of the deep region, the magnitude or direction of the inner wall gradient, the imaging distance, the degree of defocus, the degree of motion blur, etc.) in the intraductal imaging situation analyzing unit 12 in a predetermined acceptable error range. In actual operation, the same analysis (which may be mechanical or manual) as the intraductal imaging situation analysis can be performed on a plurality of images obtained beforehand and, after specifying the image of each analysis result, the parameter corresponding to each analysis result can be generated using training data from the image of the analysis result and a plurality of specific region discrimination indices can be calculated using them.

For example, to detect a specific region in an image of a ductal inner wall captured obliquely, a discrimination parameter generated using training data of a specific region shown in an image of a ductal inner wall captured obliquely is suitable. To detect a specific region in an image of a ductal inner wall captured from the front, a discrimination parameter generated using training data of a specific region shown in an image of a ductal inner wall captured from the front is suitable. Regarding the intraductal imaging situation such as the differences in the ductal deep region and the inner wall gradient direction, the imaging distance, the degree of defocus, and the degree of motion blur, a discrimination parameter generated using training data in its identical intraductal imaging situation is suitable. In the case where a plurality of intraductal imaging situations take place in combination, a discrimination parameter generated using training data in such a intraductal imaging situation combination is most suitable. In the third Embodiment, the discriminator-specific discriminating unit 131 generates a plurality of discrimination parameters depending on the difference in intraductal imaging situation beforehand, and calculates specific region discrimination indices by these discrimination parameters for the feature values (feature vectors) obtained from the feature value calculation regions.

The parameter storage unit 111 in the storage unit 11 stores discrimination parameters generated based on a plurality of pieces of training data corresponding to a plurality of intraductal imaging situations, in association with the intraductal imaging situations. Alternatively, the discrimination parameters may be stored in an external device, where the integral determining unit 132 acquires the discrimination parameters from the external device.

Figure 28:
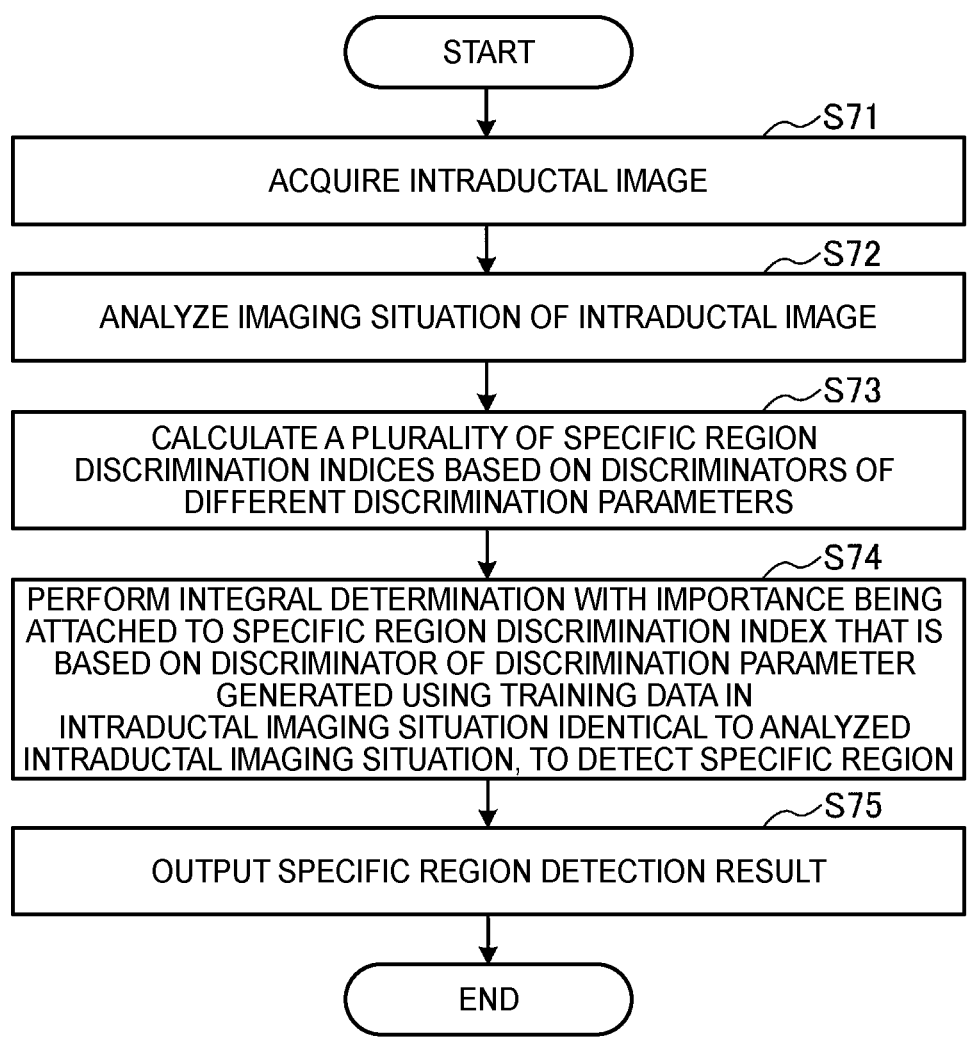
FIG. 28 is a flowchart illustrating the process performed by the image processing device according to the third Embodiment.

FIG. 28 is a flowchart illustrating the process performed by the image processing device 9. First in step S71, the arithmetic unit 10 acquires the intraductal image to be processed.

Next in step S72, the intraductal imaging situation analyzing unit 12 analyzes the imaging situation of the intraductal image.

Continue to step S73, the discriminator-specific discriminating unit 131 calculates the plurality of specific region discrimination indices based on the discriminators different in discrimination parameter.

Following this operation, the integral determining unit 132 extracts a discrimination parameter generated using training data in an intraductal imaging situation identical to the analyzed intraductal imaging situation from the parameter storage unit 111, and performs integral determination while attaching importance to the specific region discrimination index that is based on the discriminator of the discrimination parameter, to detect the specific region as noted in step S74.

Finally, in step S75, the arithmetic unit 10 outputs the specific region detection result. The image processing device 9 thus completes the series of processes. The intraductal imaging situation analysis process in step S72 and the specific region discrimination index calculation process in step S73 may be performed in reverse order or concurrently.

According to the third Embodiment described above, the plurality of specific region discrimination indices based on the discriminators different in discrimination parameter can be integrally determined depending on the intraductal imaging situation. Given that the image varies due to the difference in intraductal imaging situation, the specific region can be detected accurately by attaching importance to the specific region discrimination index that is based on the more effective feature value.

The integral determining unit 132 may further perform the integral determination described in the respective first and second Embodiments.

Figure 29:
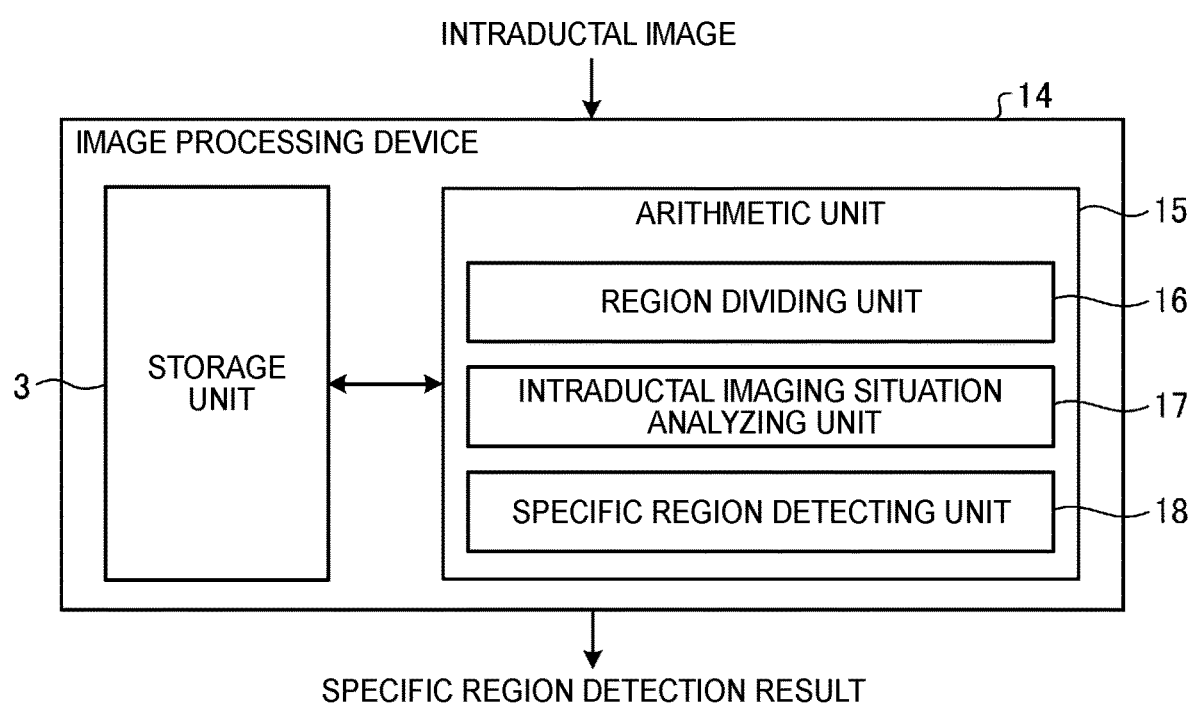
FIG. 29 is a block diagram illustrating the functional structure of an image processing device according to a fourth Embodiment.

FIG. 29 is a block diagram illustrating the functional structure of an image processing device according to the fourth Embodiment. In an image processing device 14 illustrated in FIG. 29, the structural elements having the same functions as those in the image processing device 1 illustrated in FIG. 3 are given the same reference signs as in FIG. 3.

The image processing device 14 includes an arithmetic unit 15 and the storage unit 3. The arithmetic unit 15 includes a region dividing unit 16, an intraductal imaging situation analyzing unit 17, and a specific region detecting unit 18.

The region dividing unit 16 divides the intraductal image into regions. Available region division methods include rectangular division in a predetermined size and edge-based region division. The region division methods are more fully explained in applicant's prior Japanese Patent Application No. 2012-238041). In the case of rectangular division, the intraductal image may be divided into rectangles that overlap in part.

The intraductal imaging situation analyzing unit 17 may be any one of the intraductal imaging situation analyzing units described in Embodiments 1 and 2, or any combination thereof.

The specific region detecting unit 18 may be any one of the specific region detecting units described in Embodiments 1 to 3, or any combination thereof.

FIG. 30 is a flowchart illustrating the process performed by the image processing device 14. Beginning in step S81, the arithmetic unit 15 acquires the intraductal image to be processed.

Next in step S82, the region dividing unit 16 divides the intraductal image into regions.

Next in step S83, the intraductal imaging situation analyzing unit 17 then analyzes the intraductal imaging situation in each region.

Next in step S84, the specific region detecting unit 18 calculates the plurality of specific region discrimination indices in each region.

Next in step S85, the specific region detecting unit 18 then performs integral determination on the specific region discrimination indices depending on the intraductal imaging situation to detect the specific region, in each region.

Finally, in step S86, the arithmetic unit 15 outputs the specific region detection result. The image processing device 14 thus completes the series of processes. The intraductal imaging situation analysis process in step S83 and the specific region discrimination index calculation process in step S84 may be performed in reverse order or concurrently.

According to the fourth Embodiment described above, the specific region can be detected accurately by detecting the specific region depending on the intraductal imaging situation for each region.

While the various embodiments have been described hereinabove, the present disclosure is not limited to the four Embodiments disclosed hereinabove. For example, the present disclosure may be used not only for endoscopic images for living bodies, but also for intraluminal images of virtual endoscopes in computed tomographic colonography or intraductal images captured by industrial endoscopes.

Thus, it would be obvious to those skilled in the art that various other changes and modifications can be made without departing from the spirit and scope of the invention. It is therefore intended to cover in the appended claims all such changes and modifications that are within the scope of this invention.

Example embodiments of the disclosure relate to an image processing device. The device comprises an intraductal imaging situation analyzing unit, a specific region detecting unit. The intraductal imaging situation analyzing unit analyzes, in an intraductal image which is an image of inside of a duct, an intraductal imaging situation determined based on a relationship between a subject and a part that captures an image of the subject. The specific region detecting unit calculates a plurality of specific region discrimination indices for the intraductal image, and detects a specific region by integral determination on the plurality of specific region discrimination indices depending on the intraductal imaging situation.

The specific region detecting unit can comprise a feature range-specific discriminating unit and an integral determining unit. The feature range-specific discriminating unit can calculate the plurality of specific region discrimination indices based on feature values calculated from a plurality of regions different in range. The integral determining unit can perform the integral determination while changing, depending on the intraductal imaging situation, a specific region discrimination index to be attached importance from among the plurality of specific region discrimination indices.

The intraductal imaging situation analyzing unit can comprise at least one of ductal deep region detecting unit and an inner wall gradient calculating unit. The ductal deep region detecting unit can detect a ductal deep region in the intraductal image. The inner wall gradient calculating unit can calculate a gradient of a ductal inner wall in the intraductal image. The integral determining unit can perform the integral determination while changing, depending on at least one of presence or absence of the ductal deep region and the gradient of the ductal inner wall, the specific region discrimination index to be attached importance.

The integral determining unit can attach importance to the specific region discrimination index that is based on a feature value of a larger calculation range, in the case where the ductal deep region is present than in the case where the ductal deep region is absent.

The integral determining unit can attach importance to the specific region discrimination index that is based on a feature value of a larger calculation range, in the case where the gradient of the ductal inner wall is not less than a threshold than in the case where the gradient of the ductal inner wall is less than the threshold.

The intraductal imaging situation analyzing unit can comprise at least one of an imaging distance estimating unit, a defocus analyzing unit, and a motion blur analyzing unit. The imaging distance estimating unit can estimate an imaging distance to a ductal inner wall in the intraductal image. The defocus analyzing unit can analyze a state of defocus of the intraductal image. The motion blur analyzing unit can analyze a state of motion blur of the intraductal image. The integral determining unit can perform the integral determination while changing, depending on at least one of the imaging distance, the state of defocus, and the state of motion blur, the specific region discrimination index to be attached importance.

The integral determining unit can attach importance to the specific region discrimination index that is based on a feature value of a larger calculation range, in the case where the imaging distance is longer, a degree of the defocus is larger, or a degree of the motion blur is larger.

The specific region detecting unit can comprise a shape/direction-specific discriminating unit and an integral determining unit. The shape/direction-specific discriminating unit can calculate the plurality of specific region discrimination indices based on feature values calculated from a plurality of regions different in at least one of shape and direction. The integral determining unit can perform the integral determination while changing, depending on the intraductal imaging situation, a specific region discrimination index to be attached importance from among the plurality of specific region discrimination indices.

The intraductal imaging situation analyzing unit can comprise at least one of a ductal deep region detecting unit and an inner wall gradient calculating unit. The ductal deep region detecting unit can detect a ductal deep region in the intraductal image. The inner wall gradient calculating unit can calculate a gradient of a ductal inner wall in the intraductal image. The integral determining unit can perform the integral determination while changing, depending on at least one of a direction of the ductal deep region and a direction of the gradient of the ductal inner wall, the specific region discrimination index to be attached importance.

The integral determining unit can attach importance to the specific region discrimination index that is based on a feature value of a calculation region whose shape is longer in a direction orthogonal to the direction of the ductal deep region or to the direction of the gradient of the ductal inner wall.

The intraductal imaging situation analyzing unit can comprise a motion blur analyzing unit that analyzes a state of motion blur of the intraductal image. The integral determining unit can perform the integral determination while changing, depending on the state of motion blur, the specific region discrimination index to be attached importance.

The specific region detecting unit can comprise a feature type-specific discriminating unit and an integral determining unit. The feature type-specific discriminating unit can calculate the plurality of specific region discrimination indices based on feature values different in type including color, contour, pixel value surface shape, and texture. The integral determining unit can perform the integral determination while changing, depending on the intraductal imaging situation, a specific region discrimination index to be attached importance from among the plurality of specific region discrimination indices.

The intraductal imaging situation analyzing unit can comprise at least one of a ductal deep region detecting unit and an inner wall gradient calculating unit. The ductal deep region detecting unit can detect a ductal deep region in the intraductal image. The inner wall gradient calculating unit can calculate a gradient of a ductal inner wall in the intraductal image. The integral determining unit can perform the integral determination while changing, depending on at least one of presence or absence of the ductal deep region and the gradient of the ductal inner wall, the specific region discrimination index to be attached importance.

The integral determining unit can attach importance to the specific region discrimination index that is based on a contour feature value, in the case where the ductal deep region is present or the gradient of the ductal inner wall is not less than a predetermined value.

The integral determining unit can attach importance to the specific region discrimination index that is based on a pixel value surface shape feature value or a texture feature value, in the case where the ductal deep region is absent or the gradient of the ductal inner wall is less than a predetermined value.

The intraductal imaging situation analyzing unit can comprise at least one of an imaging distance estimating unit, a defocus analyzing unit, and a motion blur analyzing unit. The imaging distance estimating unit can estimate an imaging distance to a ductal inner wall in the intraductal image. The defocus analyzing unit can analyze a state of defocus of the intraductal image. The motion blur analyzing unit can analyze a state of motion blur of the intraductal image. The integral determining unit can perform the integral determination while changing, depending on at least one of the imaging distance, the state of defocus, and the state of motion blur, the specific region discrimination index to be attached importance.

The integral determining unit can attach importance to the specific region discrimination index that is based on a color feature value or a pixel value surface shape feature value, in the case where the imaging distance is long, a degree of the defocus is not less than a predetermined degree, or a degree of the motion blur is not less than a predetermined degree.

The integral determining unit can attach importance to the specific region discrimination index that is based on a texture feature value, in the case where the imaging distance is short, a degree of the defocus is less than a predetermined degree, or a degree of the motion blur is less than a predetermined degree.

The specific region detecting unit can comprise a discriminator-specific discriminating unit and an integral determining unit. The discriminator-specific discriminating unit can calculate the plurality of specific region discrimination indices based on a plurality of different discriminators. The integral determining unit can perform the integral determination while changing, depending on the intraductal imaging situation, a specific region discrimination index to be attached importance from among the plurality of specific region discrimination indices.

The integral determining unit can attach importance to the specific region discrimination index that is based on a discriminator of a discrimination parameter generated using training data in an intraductal imaging situation identical to the analyzed intraductal imaging situation.

The image processing device can further comprise a region dividing unit that divides the intraductal image into regions. The specific region detecting unit can detect the specific region by the integral determination on the plurality of specific region discrimination indices depending on the intraductal imaging situation, for each of the regions generated as a result of the division by the region dividing unit.

Example embodiment of the present disclosure relate to an image processing method. The image processing method comprises an intraductal imaging situation analyzing step of analyzing, in an intraductal image which is an image of inside of a duct, an intraductal imaging situation determined based on a relationship between a subject and a part that captures an image of the subject; and a specific region detecting step of calculating a plurality of specific region discrimination indices for the intraductal image, and detecting a specific region by integral determination on the plurality of specific region discrimination indices depending on the intraductal imaging situation.

Example embodiment of the present disclosure relate to an image processing program for causing a computer to execute an intraductal imaging situation analyzing step of analyzing, in an intraductal image which is an image of inside of a duct, an intraductal imaging situation determined based on a relationship between a subject and a part that captures an image of the subject and a specific region detecting step of calculating a plurality of specific region discrimination indices for the intraductal image, and detecting a specific region by integral determination on the plurality of specific region discrimination indices depending on the intraductal imaging situation.

Example embodiments of the present disclosure relate to an image processing apparatus comprising at least one processor configured to perform operations of:

analyzing, in an intraductal image which is an image of inside of a duct, an intraductal imaging situation based on a position of a subject relative to a part that captures an image of the subject;

calculating a plurality of specific region discrimination indices for the intraductal image; and detecting a specific region by integral determination on the plurality of specific region discrimination indices depending on the intraductal imaging situation.

The processor can be configured to perform operations of:
calculating the plurality of specific region discrimination indices based on feature values calculated from a plurality of regions different in range; and
performing the integral determination by changing, depending on the intraductal imaging situation, a weight of a specific region discrimination index from among the plurality of specific region discrimination indices.

The processor can be configured to perform at least one of operations of:
judging whether a ductal deep region is present or absent in the intraductal image; and
calculating a gradient of a ductal inner wall in the intraductal image.

The processor can be configured to perform an operation of performing the integral determination by changing, depending on at least one of presence or absence of the ductal deep region and the gradient of the ductal inner wall, the weight of the specific region discrimination index.

The processor can be configured to perform an operation of attaching a higher weight to the specific region discrimination index that is relating to a feature value of a larger calculation range, in the case where the ductal deep region is present than in the case where the ductal deep region is absent.

The processor can be configured to perform an operation of attaching a higher weight to the specific region discrimination index that is relating to a feature value of a larger calculation range, in the case where the gradient of the ductal inner wall is not less than a threshold than in the case where the gradient of the ductal inner wall is less than the threshold.

The processor can be configured to perform at least one of operations of:
estimating an imaging distance to a ductal inner wall in the intraductal image;
analyzing a state of defocus of the intraductal image; and
analyzing a state of motion blur of the intraductal image.

The processor can be configured to perform an operation of performing the integral determination by changing, depending on at least one of the imaging distance, the state of defocus, and the state of motion blur, the weight of the specific region discrimination index.

The processor can be configured to perform operation of attaching a higher weight to the specific region discrimination index that is relating to a feature value of a larger calculation range, in the case where the imaging distance is longer, a degree of the defocus is larger, or a degree of the motion blur is larger.

The processor can be configured to perform operations of:
calculating the plurality of specific region discrimination indices relating to feature values calculated from a plurality of regions different in at least one of shape and direction; and
performing the integral determination by changing, depending on the intraductal imaging situation, a weight of a specific region discrimination index from among the plurality of specific region discrimination indices.

The processor can be configured to perform at least one of operations of:
detecting a direction of a ductal deep region in the intraductal image; and
calculating a direction of a gradient of a ductal inner wall in the intraductal image.

The processor can be configured to perform operations of performing the integral determination by changing, depending on at least one of the direction of the ductal deep region and the direction of the gradient of the ductal inner wall, the weight of the specific region discrimination index.

The processor can be configured to perform an operation of attaching higher weight to the specific region discrimination index that is relating to a feature value of a calculation region whose shape is longer in a direction orthogonal to the direction of the ductal deep region or to the direction of the gradient of the ductal inner wall.

The processor can be configured to perform operations of:
analyzing a state of motion blur of the intraductal image, and
performing the integral determination by changing, depending on the state of motion blur, the weight of the specific region discrimination index.

The processor can be configured to perform operations of:
calculating the plurality of specific region discrimination indices relating to feature values different in type including color, contour, pixel value surface shape, and texture; and
performing the integral determination by changing, depending on the intraductal imaging situation, a weight of a specific region discrimination index from among the plurality of specific region discrimination indices.

The processor can be configured to perform at least one of operations of:
judging whether a ductal deep region is present or absent in the intraductal image; and
calculating a gradient of a ductal inner wall in the intraductal image.

The processor can be configured to perform an operation of performing the integral determination by changing, depending on at least one of presence or absence of the ductal deep region and the gradient of the ductal inner wall, the weight of the specific region discrimination index.

The processor can be configured to perform an operation of attaching a higher weight to the specific region discrimination index that is relating to a contour feature value, in the case where the ductal deep region is present or the gradient of the ductal inner wall is not less than a predetermined value.

The processor can be configured to perform an operation of attaching a higher weight to the specific region discrimination index that is relating to a pixel value surface shape feature value or a texture feature value, in the case where the ductal deep region is absent or the gradient of the ductal inner wall is less than a predetermined value.

The processor can be configured to perform at least one of operations of:
estimating an imaging distance to a ductal inner wall in the intraductal image;
analyzing a state of defocus of the intraductal image; and
analyzing a state of motion blur of the intraductal image.

The processor can be configured to perform an operation of performing the integral determination by changing, depending on at least one of the imaging distance, the state of defocus, and the state of motion blur, the weight of the specific region discrimination index.

The processor can be configured to perform an operation of attaching a higher weight to the specific region discrimination index that is relating to a color feature value or a pixel value surface shape feature value, in the case where the imaging distance is not less than a predetermined degree, a degree of the defocus is not less than a predetermined degree, or a degree of the motion blur is not less than a predetermined degree.

The processor can be configured to perform an operation of attaching a higher weight to the specific region discrimination index that is relating to a texture feature value, in the case where the imaging distance is less than a predetermined degree, a degree of the defocus is less than a predetermined degree, or a degree of the motion blur is less than a predetermined degree.

The processor can be configured to perform operations of:
calculating the plurality of specific region discrimination indices based on a plurality of different discriminators; and
performing the integral determination by changing, depending on the intraductal imaging situation, a weight of a specific region discrimination index from among the plurality of specific region discrimination indices.

The processor can be configured to perform an operation of attaching a higher weight to the specific region discrimination index that is based on a discriminator of a discrimination parameter generated using training data in an intraductal imaging situation identical to the analyzed intraductal imaging situation.

The processor can be configured to perform operations of:
dividing the intraductal image into regions; and
detecting the specific region by the integral determination on the plurality of specific region discrimination indices depending on the intraductal imaging situation, for each of the regions generated as a result of the division.

Example embodiments of the present disclosure relate to a method comprising:
analyzing, in an intraductal image which is an image of inside of a duct, an intraductal imaging situation based on a position of a subject relative to a part that captures an image of the subject;
calculating a plurality of specific region discrimination indices for the intraductal image: and
detecting a specific region by integral determination on the plurality of specific region discrimination indices depending on the intraductal imaging situation.

Example embodiments of the present disclosure relate to a computer program product including a non-transitory computer readable medium having computer program code encoded thereon that when executed by a processor of a computer causes computer to perform image process, the computer program code comprising:
computer program code for analyzing, in an intraductal image which is an image of inside of a duct, an intraductal imaging situation based on a position of a subject relative to a part that captures an image of the subject;
computer program code for calculating a plurality of specific region discrimination indices for the intraductal image; and
computer program code for detecting a specific region by integral determination on the plurality of specific region discrimination indices depending on the intraductal imaging situation.

Example embodiments of the present disclosure relates to an endoscopic imaging system comprising: an image processing device having
an intraductal imaging situation analyzing unit being configured to analyzes, an intraductal image situation which is an image of inside of a duct wherein the intraductal imaging situation is determined based on a relationship between a subject and a part that captures an image of the subject, and
a specific region detecting unit being used to calculate a plurality of specific region discrimination indices for the intraductal image situation and detects a specific region by integral determination on the plurality of specific region discrimination indices depending on the intraductal imaging situation.

The image processing device of the endoscopic imaging system includes at least one processor configured to execute specific functions and operation of the endoscopic imaging system.

The intraductal imaging situation of the endoscopic imaging system is divided into regions to detect the specific region by the integral determination on the plurality of specific region discrimination indices depending on the intraductal imaging situation, for each of the regions generated as a result of the division by a region dividing unit.

The plurality of specific region discrimination indices of the endoscopic imaging system is calculated based on a plurality of different discriminators.

The integral determination of the endoscopic imaging system is performed by changing a weight of a specific region discrimination index from among the plurality of specific region discrimination indices.

The ductal deep region in the intraductal image of the endoscopic imaging system is detected and a gradient of a ductal inner wall in the intraductal image is calculated so as to perform the integral determination by changing, depending on at least one of presence or absence of the ductal deep region and the gradient of the ductal inner wall, the specific region discrimination index.

The endoscopic imaging system operates such that a greater weight is assigned to the specific region discrimination index based on a feature value of a larger calculation range where the ductal deep region is present.

The endoscopic imaging system operates such that a greater weight is assigned to the specific region discrimination index based on a feature value of a larger calculation range, in the case where the gradient of the ductal inner wall is not less than a threshold.

The endoscopic imaging system operates such that the plurality of specific region discrimination indices is calculated based on features values calculated from a plurality of regions different in range and wherein the integral determination is performed by changing a weight of a specific region discrimination index from among the plurality of specific region discrimination indices.

The endoscopic imaging system operates such that an image distance to a ductal inner wall in the intraductal image is estimated and a state of defocus or state of motion blur of the intraductal image is analyzed so as to perform the integral determination by changing, depending on at least one of the imaging distance, the state of defocus, and the state of motion blur, the weight of the specific region discrimination index.

The endoscopic imaging system operates such that a weight is assigned to the specific region discrimination index based on a feature value of a larger calculation range, in the case where the imaging distance is longer, a degree of the defocus is larger, or a degree of the motion blur is larger.

What is claimed is:
1. An image processing device comprising:
at least one processor comprising hardware, wherein the hardware is configured to implement:
analyzing, in an intraductal image which is an image of inside of a duct, an intraductal imaging situation based on a position of a subject relative to a part that captures an image of the subject;
calculating a plurality of specific region discrimination indices for the intraductal image;
detecting a specific region by integral determination on the plurality of specific region discrimination indices depending on the intraductal imaging situation;

calculating the plurality of specific region discrimination indices based on a plurality of different discriminators; and performing the integral determination by changing, depending on the intraductal imaging situation, a weight of a specific region discrimination index from among the plurality of specific region discrimination indices.

2. The image processing device according to claim 1, wherein the hardware is further configured to implement:
calculating the plurality of specific region discrimination indices based on feature values calculated from a plurality of regions different in range; and
performing the integral determination by changing, depending on the intraductal imaging situation, a weight of a specific region discrimination index among the plurality of specific region discrimination indices.

3. The image processing device according to claim 2, wherein the hardware further configured to implement at least one of:
estimating an imaging distance to a ductal inner wall in the intraductal image;
analyzing a state of defocus of the intraductal image;
analyzing a state of motion blur of the intraductal image; and
performing the integral determination by changing, depending on at least one of the imaging distance, the state of defocus, and the state of motion blur, the weight of the specific region discrimination index.

4. The image processing device according to claim 3, wherein the hardware further configured to implement attaching weight to the specific region discrimination index that is based on a feature value of a larger calculation range, in the case where the imaging distance is longer, a degree of the defocus is larger, or a degree of the motion blur is larger.

5. The image processing device according to claim 2, wherein the hardware is configured to further implement at least one of:
detecting a ductal deep region in the intraductal image;
calculating a gradient of a ductal inner wall in the intraductal image; and
performing the integral determination by changing, depending on at least one of presence or absence of the ductal deep region and the gradient of the ductal inner wall, the specific region discrimination index.

6. The image processing device according to claim 5, wherein the hardware is configured to implement attaching a greater weight to the specific region discrimination index based on a feature value of a larger calculation range where the ductal deep region is present.

7. The image processing device according to claim 5, wherein the hardware is further configured to implement attaching a greater weight to the specific region discrimination index that is based on a feature value of a larger calculation range, in the case where the gradient of the ductal inner wall is not less than a threshold.

8. The image processing device according to claim 1, wherein the hardware further configured to implement:
calculating the plurality of specific region discrimination indices based on feature values calculated from a plurality of regions different in at least one of shape and direction; and
performing the integral determination by changing, depending on the intraductal imaging situation, a weight of a specific region discrimination index to be attached importance from among the plurality of specific region discrimination indices.

9. The image processing device according to claim 8, wherein the hardware further configured to implement
analyzing a state of motion blur of the intraductal image, and
performing the integral determination by changing, depending on the state of motion blur, the weight of the specific region discrimination index.

10. The image processing device according to claim 8, wherein the hardware further configured to implement at least one of:
detecting direction of a ductal deep region in the intraductal image;
calculating a direction of a gradient of a ductal inner wall in the intraductal image; and
performing the integral determination by changing, depending on at least one of the direction of the ductal deep region and the direction of the gradient of the ductal inner wall, the weight of the specific region discrimination index.

11. The image processing device according to claim 10, wherein the hardware further configured to implement attaching greater weight to the specific region discrimination index based on a feature value of a calculation region whose shape is longer in a direction orthogonal to the direction of the ductal deep region or to the direction of the gradient of the ductal inner wall.

12. The image processing device according to claim 1, wherein the hardware further configured to implement:
calculating the plurality of specific region discrimination indices based on feature values different in type including color, contour, pixel value surface shape, and texture; and
performing the integral determination by changing, depending on the intraductal imaging situation, a weight of a specific region discrimination index from among the plurality of specific region discrimination indices.

13. The image processing device according to claim 12, wherein the hardware further configured to implement at least one of:
configuring whether a ductal deep region in the intraductal image is present or absent;
calculating a gradient of a ductal inner wall in the intraductal image; and
performing the integral determination by changing, depending on at least one of presence or absence of the ductal deep region and the gradient of the ductal inner wall, the weight of the specific region discrimination index.

14. The image processing device according to claim 13, wherein the hardware further configured to implement:
attaching a greater weight to the specific region discrimination index based on a contour feature value, in the case where the ductal deep region is present or the gradient of the ductal inner wall is not less than a predetermined value.

15. The image processing device according to claim 13, wherein the hardware further configured to implement:
attaching greater weight to the specific region discrimination index based on a pixel value surface shape feature value or a texture feature value, in the case where the ductal deep region is absent or the gradient of the ductal inner wall is less than a predetermined value.

16. The image processing device according to claim 12, wherein the hardware further configured to implement at least one of:
estimating an imaging distance to a ductal inner wall in the intraductal image;

analyzing a state of defocus of the intraductal image;
analyzing a state of motion blur of the intraductal image; and
performing the integral determination by changing, depending on at least one of the imaging distance, the state of defocus, and the state of motion blur, the weight of the specific region discrimination index.

17. The image processing device according to claim 16, wherein the hardware further configured to implement: attaching a greater weight to the specific region discrimination index that is based on a color feature value or a pixel value surface shape feature value, in the case where the imaging distance is not less than a predetermined value, a degree of the defocus is not less than a predetermined degree, or a degree of the motion blur is not less than a predetermined degree.

18. The image processing device according to claim 16, wherein the hardware further configured to implement: attaching greater weight to the specific region discrimination index based on a texture feature value, in the case where the imaging distance is less than a predetermined value, a degree of the defocus is less than a predetermined degree, or a degree of the motion blur is less than a predetermined degree.

19. The image processing device according to claim 1, wherein the hardware further configured to implement: attaching a greater weight to the specific region discrimination index based on a discrimination parameter generated using training data in an intraductal imaging situation identical to the analyzed intraductal imaging situation.

20. The image processing device according to claim 1, wherein the hardware further configured to implement:
dividing the intraductal image into regions; and
detecting the specific region by the integral determination on the plurality of specific region discrimination indices depending on the intraductal imaging situation, for each of the regions generated as a result of the division by the region dividing unit.

21. An image processing method comprising:
at least one processor comprising hardware, executing:
analyzing, in an intraductal image which is an image of inside of a duct, an intraductal imaging situation based on a relationship between a subject and a part that captures an image of the subject; and
calculating a plurality of specific region discrimination indices for the intraductal image; and
detecting a specific region by integral determination on the plurality of specific region discrimination indices depending on the intraductal imaging situation.

22. A non-transitory image processing program product having computer program code encoded thereon that when executed by a processor of a computer causes the computer to perform the operations of:
analyzing, in an intraductal image which is an image of inside of a duct, an intraductal imaging situation based on a position of a subject relative to a part that captures an image of the subject;
calculating a plurality of specific region discrimination indices for the intraductal image;
detecting a specific region by integral determination on the plurality of specific region discrimination indices depending on the intraductal imaging situation;
calculating the plurality of specific region discrimination indices based on a plurality of different discriminators; and
performing the integral determination by changing, depending on the intraductal imaging situation, a weight of a specific region discrimination index from among the plurality of specific region discrimination indices.

* * * * *